US010386442B2

(12) United States Patent
Bannae

(10) Patent No.: US 10,386,442 B2
(45) Date of Patent: Aug. 20, 2019

(54) MAGNETIC RESONANCE IMAGING APPARATUS AND METHOD CONTROLLING EXECUTION OF A PULSE SEQUENCE BASED ON RECOVERY OF LONGITUDINAL MAGNETIZATION OF A MONITOR REGION

(71) Applicant: Canon Medical Systems Corporation, Otawara-shi (JP)

(72) Inventor: Shuhei Bannae, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 154 days.

(21) Appl. No.: 15/177,432

(22) Filed: Jun. 9, 2016

(65) Prior Publication Data

US 2017/0097401 A1 Apr. 6, 2017

(30) Foreign Application Priority Data

Oct. 5, 2015 (JP) .................................. 2015-197889

(51) Int. Cl.
*G01R 33/54* (2006.01)
*A61B 5/02* (2006.01)
(Continued)

(52) U.S. Cl.
CPC ........ *G01R 33/5673* (2013.01); *A61B 5/0402* (2013.01); *A61B 5/055* (2013.01);
(Continued)

(58) Field of Classification Search
CPC .............. G01R 33/543; G01R 33/5602; G01R 33/5673; G01R 33/5676; G01R 33/4835; A61B 5/0402; A61B 5/7285; A61B 5/055
See application file for complete search history.

(56) References Cited

U.S. PATENT DOCUMENTS

2002/0032376 A1* 3/2002 Miyazaki ............. A61B 5/0263
600/410
2007/0092123 A1 4/2007 Popescu
(Continued)

FOREIGN PATENT DOCUMENTS

JP 2004-329669 11/2004
JP 2006-320527 A 11/2006
(Continued)

OTHER PUBLICATIONS

Office Action dated May 14, 2019, in Japanese Patent Application No. 2015-197889, filed Oct. 5, 2015.

*Primary Examiner* — Minh N Tang
(74) *Attorney, Agent, or Firm* — Oblon, McClelland, Maier & Neustadt, L.L.P.

(57) ABSTRACT

A Magnetic Resonance Imaging apparatus according to an embodiment includes processing circuitry. The processing circuitry is configured to execute a pulse sequence to acquire data from an image taking region after applying a pre-pulse in synchronization with a predetermined electrocardiographic waveform of the subject. The processing circuitry is configured to monitor recovery of longitudinal magnetization by acquiring data from a monitor region that is different from the image taking region, by using timing linked with the timing with which the pre-pulse is applied. The processing circuitry is configured to control execution of the pulse sequence on the basis of a signal value of the data from the monitor region.

11 Claims, 11 Drawing Sheets

(51) Int. Cl.
    *G01R 33/567* (2006.01)
    *A61B 5/0402* (2006.01)
    *A61B 5/00* (2006.01)
    *G01R 33/56* (2006.01)
    *A61B 5/055* (2006.01)

(52) U.S. Cl.
    CPC .......... *A61B 5/7285* (2013.01); *G01R 33/543* (2013.01); *G01R 33/5602* (2013.01)

(56) References Cited

U.S. PATENT DOCUMENTS

| | | | | |
|---|---|---|---|---|
| 2013/0253307 A1* | 9/2013 | Miyazaki | ........... | G01R 33/5635 600/419 |
| 2014/0159720 A1* | 6/2014 | Markl | ................ | G01R 33/4835 324/309 |
| 2015/0153434 A1* | 6/2015 | Ooshima | ........... | G01R 33/5676 324/309 |

FOREIGN PATENT DOCUMENTS

| | | |
|---|---|---|
| JP | 2007-111535 | 5/2007 |
| JP | 2008-86343 | 4/2008 |
| WO | WO 2005/023107 A1 | 3/2005 |

* cited by examiner

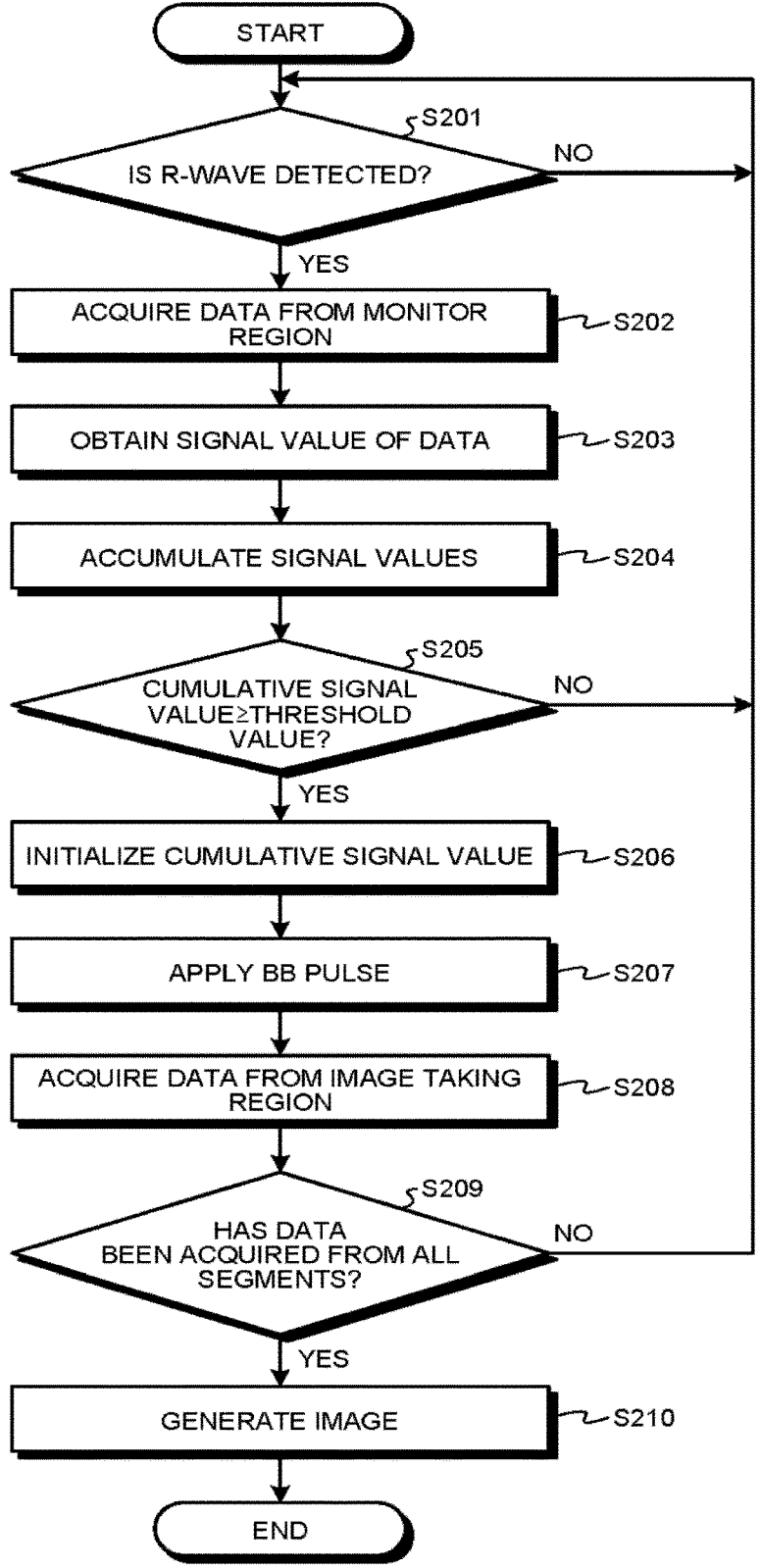

MAGNETIC RESONANCE IMAGING APPARATUS AND METHOD CONTROLLING EXECUTION OF A PULSE SEQUENCE BASED ON RECOVERY OF LONGITUDINAL MAGNETIZATION OF A MONITOR REGION

CROSS-REFERENCE TO RELATED APPLICATIONS

This application is based upon and claims the benefit of priority from Japanese Patent Application No. 2015-197689, filed on Oct. 5, 2015; the entire contents of which are incorporated herein by reference.

FIELD

Embodiments described herein relate generally to magnetic resonance imaging apparatus and method.

BACKGROUND

Conventionally, an image taking method is known by which, during an image taking process performed by a magnetic resonance imaging apparatus, data is acquired in synchronization with a predetermined electrocardiographic waveform of the examined subject. Further, another image taking method is also known by which, similarly during an image taking process performed by a magnetic resonance imaging apparatus, data is acquired from an image taking region after applying a pre-pulse that changes longitudinal magnetization of a nuclear spin into a negative value. By using this method, because the data is acquired at the time when the longitudinal magnetization of a predetermined tissue has recovered up to a level close to zero after the pre-pulse is applied, it is possible to obtain an image in which the signal value of the tissue is suppressed.

In this situation, when the abovementioned image taking process performed in synchronization with the electrocardiographic waveform is used together with the image taking process using the pre-pulse, when the cardiac cycle is disturbed by arrhythmia or the like, there may be seine situations in which the time at which the longitudinal magnetization of the tissue recovers up to the level close to zero is different from the time at which the data acquiring process is performed. In those situations, the acquired data may have inappropriate data mixed therein, and the quality of the generated image may be degraded.

BRIEF DESCRIPTION OF THE DRAWINGS

FIG. 14 is a flowchart illustrating a processing procedure according to an image taking method implemented by an MRI apparatus according to the fourth embodiment.

DETAILED DESCRIPTION

A Magnetic Resonance Imaging (MRI) apparatus according to an embodiment includes processing circuitry. The processing circuitry is configured to execute a pulse sequence to acquire data from an image taking region after applying a pre-pulse in synchronization with a predetermined electrocardiographic waveform of the subject. The processing circuitry is configured to monitor recovery of longitudinal magnetization by acquiring data from a monitor region that is different from the image taking region, by using timing linked with the timing with which the pre-pulse is applied. The processing circuitry is configured to control execution of the pulse sequence on the basis of a signal value of the data from the monitor region.

Exemplary embodiments of the MRI apparatus will be explained in detail below, with reference to the accompanying drawings.

First Embodiment

Figure 1:
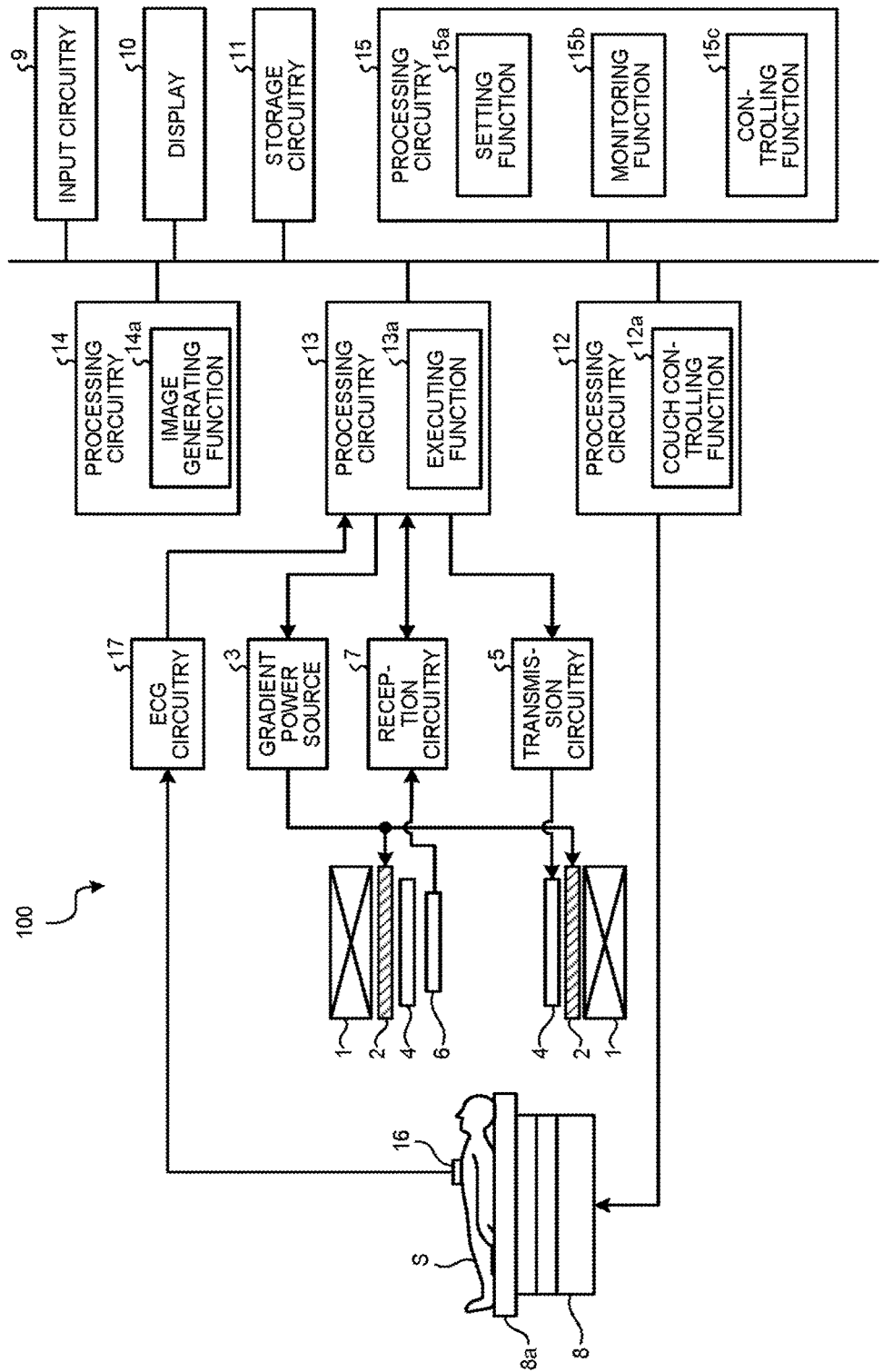
FIG. 1 is a block diagram of an exemplary configuration of a Magnetic Resonance Imaging (MRI) apparatus according to a first embodiment.

FIG. 1 is a diagram of an exemplary configuration of an MRI apparatus according to a first embodiment. For example, as illustrated in FIG. 1, an MRI apparatus 100 includes a static magnetic field magnet 1, a gradient coil 2, a gradient power source 3, a transmission coil 4, transmission circuitry 5, a reception coil 6, reception circuitry 7, a couch 8, input circuitry 9, a display 10, storage circuitry 11, processing circuitries 12 to 15, an electrocardiogram (ECG) sensor 16, and ECG circuitry 17.

The static magnetic field magnet 1 is formed to have a hollow and substantially circular cylindrical shape (which may have an oval cross-section orthogonal to the central axis thereof) and is configured to generate a static magnetic field in an image taking space formed on the inner circumferential side thereof. For example, the static magnetic field magnet 1 may be realized with a permanent magnet, a superconductive magnet, or the like.

The gradient coil 2 is formed to have a hollow and substantially circular cylindrical shape (which may have an oval cross-section orthogonal to the central axis thereof) and is disposed on the inner circumferential side of the static magnetic field magnet 1. The gradient coil 2 includes three coils configured to generate gradient magnetic fields along x-, y-, and z-axes, respectively, that are orthogonal to one another. In this situation, the x-axis, the y-axis, and the z-axis structure an apparatus coordinate system unique to the MRI apparatus 100. For example, the x-axis direction is set in the vertical direction, whereas the y-axis direction is set in the horizontal direction. Further, the z-axis direction is set so as to be the same as the direction of a magnetic flux in the static magnetic field generated by the static magnetic field magnet 1.

By individually supplying an electric current to each of the three coils included in the gradient coil 2, the gradient power source 3 is configured to cause gradient magnetic fields to be generated along the x-, y-, and z-axes, in the image taking space. The gradient power source 3 is able to cause the gradient magnetic fields to be generated along a read-out direction, a phase-encoding direction, and a slice direction that are orthogonal to one another, by generating the gradient magnetic fields along the x-, y-, and z-axes, as appropriate. In this situation, the axes extending along the read-out direction, the phase-encoding direction, and the slice direction structure a logical coordinate system used for defining slice regions or a volume region serving as a target of an image taking process. In the following sections, the gradient magnetic field generated along the read-out direction will be referred to as a read-out gradient magnetic field; the gradient magnetic field generated along the phase-encoding direction will be referred to as a phase-encoding gradient magnetic field; and the gradient magnetic field generated along the slice direction will be referred to as a slice gradient magnetic field.

The gradient magnetic fields are superimposed on the static magnetic field generated by the static magnetic field magnet 1 and are used for appending spatial position information to magnetic resonance (MR) signals. More specifically, the read-out gradient magnetic field appends position information along the read-out direction to an MR signal, by varying the frequency of the MR signal in accordance with the position in the read-out direction. Further, the phase-encoding gradient magnetic field appends position information in the phase-encoding direction to an MR signal, by varying the phase of the MR signal along the phase-encoding direction. Further, when an image taking region is represented by slice regions, the slice gradient magnetic field is used for determining the orientations, the thicknesses, and the quantity of the slice regions. In contrast, when the image taking region is represented by a volume region, the slice gradient magnetic field appends position information along the slice direction to an MR signal, by varying the phase of the MR signal in accordance with the position in the slice direction.

The transmission coil 4 is formed to have a hollow and substantially circular cylindrical shape (which may have an oval cross-section orthogonal to the central axis thereof) and is disposed on the inside of the gradient coil 2. The transmission coil 4 is configured to apply a Radio Frequency (RF) pulse output from the transmission circuitry 5 to the image taking space.

The transmission circuitry 5 is configured to output the RF pulse corresponding to a Larmor frequency to the transmission coil 4. For example, the transmission circuitry 5 includes an oscillation circuit, a phase selecting circuit, a frequency converting circuit, an amplitude modulating circuit, and an RF amplifying circuit. The oscillation circuit is configured to generate an RF pulse having a resonant frequency unique to a targeted atomic nucleus placed in the static magnetic field. The phase selecting circuit is configured to select a phase of the RF pulse output from the oscillation circuit. The frequency converting circuit is configured to convert the frequency of the RF pulse output from the phase selecting circuit. The amplitude modulating circuit is configured to modulate the amplitude of the RF pulse output from the frequency converting circuit, according to a sinc function, for example. The RF amplifying circuit is configured to amplify the RF pulse output from the amplitude modulating circuit and to output the amplified RF pulse to the transmission coil 4.

The reception coil 6 is attached to a subject S placed in the image taking space and to receive MR signals emitted from the subject S due to an influence of an RF magnetic field applied by the transmission coil 4. Further, the reception coil 6 is configured to output the received MR signals to the reception circuitry 7. For example, as the reception coil 6, an exclusive-use coil is used in correspondence with a site serving as a target of an image taking process. In this situation, examples of the exclusive-use coil include a reception coil for the head, a reception coil for the spine, and a reception coil for the abdomen.

The reception circuitry 7 is configured to generate MR signal data on the basis of the MR signals output from the reception coil 6 and to output the generated MR signal data to the processing circuitry 13. For example, the reception circuitry 7 includes a selecting circuit, a pre-amplifying circuit, a phase detecting circuit, and an analog/digital converting circuit. The selecting circuit is configured to selectively receive an input of the MR signals output from the reception coil 6. The pre-amplifying circuit is configured to amplify the MR signals output from the selecting circuit. The phase detecting circuit is configured to detect the phases of the MR signals output from the pre-amplifying circuit. The analog/digital converting circuit is configured to generate the MR signal data by converting analog signals output from the phase detecting circuit into digital signals and to output the generated MR signal data to the processing circuitry 13.

In the present example, the situation in which the transmission coil 4 applies the RF pulse so that the reception coil 6 receives the MR signals is explained; however, possible embodiments are not limited to this example. For instance, the transmission coil 4 may further have a receiving function to receive the MR signals. Further, the reception coil 6 may further have a transmitting function to apply an RF magnetic field. When the transmission coil 4 has the receiving function, the reception circuitry 7 generates MR signal data also from the MR signals received by the transmission coil 4. Further, when the reception coil 6 has the transmitting function, the transmission circuitry 5 outputs an RF pulse also to the reception coil 6.

The couch 8 includes a couchtop 8a on which the subject S is placed. When an image taking process is performed on the subject S, the couchtop 8a is inserted into the image taking space formed on the inside of the static magnetic field magnet 1 and the gradient coil 2. For example, the couch 8 is installed in such a manner that the longitudinal direction thereof extends parallel to the central axis of the static magnetic field magnet 1.

The input circuitry 9 is configured to receive operations to input various types of instructions and various types of information from an operator. For example, the input circuitry 9 is realized with a trackball, a switch button, a mouse, a keyboard, a touch panel, and/or the like. The input circuitry 9 is connected to the processing circuitry 15 and is configured to convert each of the input operations received from the operator into an electrical signal and to output the electrical signal to the processing circuitry 15.

The display 10 is configured to display various types of information and various types of images. For example, the display 10 is realized with a liquid crystal monitor, a Cathode Ray Tube (CRT) monitor, a touch panel, or the like.

The display 10 is connected to the processing circuitry 15 and is configured to convert data of the various types of information and the various types of images sent thereto from the processing circuitry 15, into display-purpose electrical signals and to output the display-purpose electrical signals.

The storage circuitry 11 is configured to store various types of data therein. For example, the storage circuitry 11 stores therein the MR signal data and image data for each subject S. For example, the storage circuitry 11 is realized with a semiconductor memory device such as a Random Access Memory (RAM), a flash memory, or the like, or a hard disk, an optical disk, or the like.

The processing circuitry 12 includes a couch controlling function 12a. For example, the processing circuitry 12 is realized with a processor. The couch controlling function 12a is connected to the couch 8 and is configured to control operations of the couch 8 by outputting a control-purpose electrical signal to the couch 8. For example, the couch controlling function 12a receives, via the input circuitry 9, an instruction to move the couchtop 8a in a longitudinal direction, an up-and-down direction, or a left-and-right direction from the operator and operates a driving mechanism for the couchtop 8a included in the couch 8 so as to move the couchtop 8a according to the received instruction.

The processing circuitry 13 is configured to execute various types of pulse sequences. For example, the processing circuitry 13 is realized with a processor. More specifically, the processing circuitry 13 executes the various types of pulse sequences by driving the gradient power source 3, the transmission circuitry 5, and the reception circuitry 7 on the basis of sequence execution data output from the processing circuitry 15.

In this situation, the sequence execution data is information that defines a pulse sequence indicating a procedure performed to acquire the MR signal data. More specifically, the sequence execution data is information that defines: the timing with which the electric current is to be supplied from the gradient power source 3 to the gradient coil 2 and the intensity of the electric current to be supplied; the intensity of an RF pulse current to be supplied from the transmission circuitry 5 to the transmission coil 4 and the timing with which the RF pulse current is to be supplied; the timing with which the MR signals are to be detected by the reception circuitry 7, and the like.

Further, as a result of executing the various types of pulse sequences, the processing circuitry 13 is configured to receive the MR signal data from the reception circuitry 7 and to store the received MR signal data into the storage circuitry 11. In this situation, a set made up of pieces of MR signal data received by the processing circuitry 13 is stored, into the storage circuitry 11, as data structuring a k-space, by being arranged either two-dimensionally or three-dimensionally in accordance with the position information appended by the read-out gradient magnetic field, the phase-encoding gradient magnetic field, and the slice gradient magnetic field described above.

The processing circuitry 14 includes an image generating function 14a. For example, the processing circuitry 14 is realized with a processor. The image generating function 14a is configured to generate an image on the basis of the MR signal data stored in the storage circuitry 11. More specifically, the image generating function 14a generates the image by reading the MR signal data stored in the storage circuitry 11 by the processing circuitry 13 and performing a post-processing process, i.e., a reconstructing process such as a Fourier transform on the read MR signal data. Further, the image generating function 14a is configured to store image data of the generated image into the storage circuitry 11.

The processing circuitry 15 is configured to exercise overall control of the MRI apparatus 100 by controlling constituent elements included in the MRI apparatus 100. For example, the processing circuitry 15 is realized with a processor. For example, the processing circuitry 15 is configured to receive, via the input circuitry 9, inputs of various types of parameters related to a pulse sequence from the operator and to generate the sequence execution data on the basis of the received parameters. After that, by transmitting the generated sequence execution data to the processing circuitry 13, the processing circuitry 15 is configured to execute the various types of pulse sequences. Further, for example, the processing circuitry 15 is configured to read the image data of an image requested by the operator from the storage circuitry 11 and to output the read image to the display 10.

The electrocardiogram (ECG) sensor 16 is attached to the surface of the body of the subject S and is configured to detect an electrocardiographic signal (hereinafter, "ECG signal") of the subject S. After that, the ECG sensor 16 is configured to output the detected ECG signal to the ECG circuitry 17.

The ECG circuitry 17 is configured to detect a predetermined electrocardiographic waveform (hereinafter "ECG waveform") on the basis of the ECG signal output from the ECG sensor 16. For example, the ECG circuitry 17 detects an R-wave as the predetermined ECG waveform. After that, the ECG circuitry 17 generates a trigger signal at the time when the predetermined ECG waveform is detected and outputs the generated trigger signal to the processing circuitry 13.

The exemplary configuration of the MRI apparatus 100 according to the first embodiment has thus been explained. The MRI apparatus 100 configured as described above implements an image taking method by which data is acquired in synchronization with a predetermined ECG waveform of the subject. Further, the MRI apparatus 100 implements an image taking method by which data is acquired from an image taking region after applying a pre-pulse that changes longitudinal magnetization of a nuclear spin into a negative value. According to this image taking method, the data is acquired at the time when longitudinal magnetization of a predetermined tissue has recovered up to a level close to zero after the pre-pulse is applied. It is therefore possible to obtain an image in which the signal value of the tissue is suppressed.

For example, when taking a T2-weighted image of the heart, the MRI apparatus 100 acquires data in synchronization with an R-wave of the subject. Further, for example, when taking a T2-weighted image of the heart, the MRI apparatus 100 suppresses the signal value of the blood in the heart chambers by using a pre-pulse called a "Black Blood (BB) pulse".

In this situation, when the abovementioned image taking process performed in synchronization with the ECG waveform is used together with the image taking process using the pre-pulse, when the cardiac cycle is disturbed by arrhythmia or the like, there may be some situations in which the time at which the longitudinal magnetization of the tissue recovers up to a level close to zero is different from the time at which the data acquiring process is performed. In those situations, the acquired data may have inappropriate data mixed therein, and the quality of the generated image may be degraded.

For example, when taking an image of the heart, it is difficult to acquire all the data required by the generation of the image during one heartbeat. Thus, it is often a common practice to acquire the data in a plurality of divided groups called "segments". For example, when the data amount required by the generation of the image is 100, and the data amount contained in each segment is 10, the data is acquired in ten divided segments. Further, for example, the first segment is acquired during the first heartbeat, the second segment is acquired during the second heartbeat, . . . , and the tenth segment is acquired during the tenth heartbeat.

Further, generally speaking, during an image taking process using a BB pulse, the signal value of blood at the point in time when the data is acquired is affected by the magnitude of longitudinal magnetization of the blood observed at the point in time when the BB pulse is applied. Accordingly, in order to arrange the signal values of the blood to be uniform among the segments, it is desirable to arrange the longitudinal magnetization of the blood to be sufficiently recovered before the application of the BB pulse so that the fluctuation of the longitudinal magnetization of the blood is in a stable state at the time of the application of the BB pulse. For this reason, generally speaking, when a BB pulse is used for an image taking process performed in synchronization with an ECG waveform, a data acquiring process is performed once every three to four heartbeats.

Figure 2:
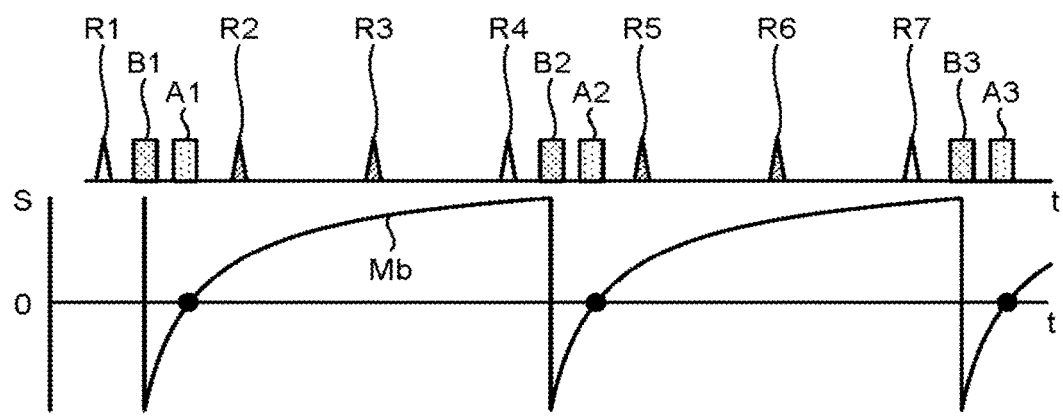
FIGS. 2 and 3 are time charts each illustrating an example of a data acquiring process in a commonly-practiced heart image taking process.
Figure 3:
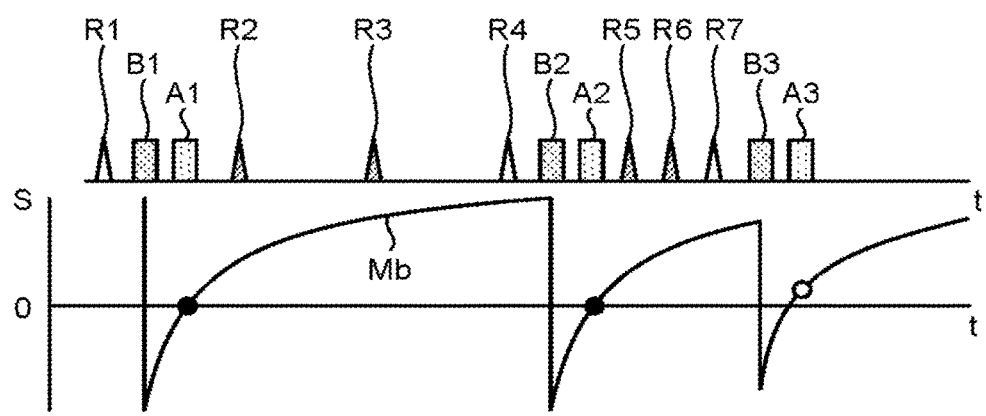

FIGS. 2 and 3 are time charts each illustrating an example of a data acquiring process in a commonly-practiced heart image taking process. FIGS. 2 and 3 illustrate the examples in which the application of a BB pulse and the data acquiring process from an image taking region are performed once every three heartbeats. Further, FIG. 2 illustrates a time chart of a situation where the subject has no arrhythmia. FIG. 3 illustrates a time chart of a situation where the intervals of the R-waves started to be shorter due to arrhythmia during the period of time.

In the present example, the diagrams in the top sections of FIGS. 2 and 3 indicate the timing of the R-waves, the pre-pulses, and the data acquiring processes. In FIGS. 2 and 3, the horizontal axis t expresses time. The reference characters R1 to R7 each indicate a time at which an R-wave is detected. The reference characters B1 to B3 each indicate a time at which a BB pulse is applied. The reference characters A1 to A3 each indicate a time at which data is acquired from the image taking region.

The charts in the bottom sections of FIGS. 2 and 3 indicate fluctuations of the signal value corresponding to the longitudinal magnetization of blood. In these charts, the horizontal axis t expresses time, which is aligned with the time in the diagram in the top section. The vertical axis S expresses the signal value. Further, the curve Mb indicates a fluctuation of the signal value corresponding to the longitudinal magnetization of the blood. The black dots on the curve Mb each indicate a time at which the signal value corresponding to the longitudinal magnetization is equal to zero.

For example, as illustrated in FIGS. 2 and 3, when the application of a BB pulse and the data acquiring process from the image taking region are performed once every three heartbeats, a BB pulse is applied (B1) and data is acquired (A1) with the first R-wave (R1). With the second and the third R-waves (R2 and R3), neither the application of a BB pulse nor the data acquiring process is performed. Further, with the fourth R-wave (R4), a BB pulse is applied (B2) and data is acquired (A2). With the fifth and the sixth R-waves (R5 and R6), neither the application of a BB pulse nor the data acquiring process is performed. Also with the seventh R-wave (R7), a BB pulse is applied (B3) and data is acquired (A3).

In this situation, the waiting time period between the time when a BB pulse is applied and the time when a data acquiring process is started is considered to be a time period it takes for the longitudinal magnetization of the blood to recover and reach a level close to zero after being inverted by the BB pulse. The waiting time period in this situation is a certain length of time determined on the basis of a longitudinal relaxation time period (which may be referred to as "T1") unique to blood, or the like.

Further, as illustrated in FIG. 2, for example, when the subject has no arrhythmia, the R-waves (R1 to R7) are detected at substantially regular intervals. Thus, the degrees of recovery of the longitudinal magnetization of the blood at the point in time when a BB pulse is applied are also substantially constant. Thus, the data acquiring processes (A1 to A3) are performed at the time when the longitudinal magnetization of the blood is at a level close to zero, as scheduled.

In contrast, as illustrated in FIG. 3, for example, when the subject has arrhythmia, the intervals between the R-waves vary. FIG. 3 illustrates the example in which the intervals of the R-waves are substantially regular during the time period from the first R-wave to the fifth R-wave (R1 to R5), and the intervals of the R-waves become shorter due to arrhythmia during the time period from the fifth R-wave to the seventh R-wave (R5 to R7). In that situation, when the application of a BB pulse and the data acquiring process from the image taking region are performed once every three heartbeats, the time period from the time when the second BB pulse (B2) is applied to the time when the third BB pulse (B3) is applied is shorter than the time period from the time when the first BB pulse (B1) is applied to the time when the second BB pulse (B2) is applied. As a result, the recovery of the longitudinal magnetization of the blood at the point of time when the third BB pulse (B3) is applied is insufficient, and the magnitude of the longitudinal magnetization of the blood observed immediately after the inversion is smaller than scheduled. For this reason, it turns out that the longitudinal magnetization of the blood recovers earlier than scheduled. Accordingly, at the time when the third data acquiring process (A3) is performed (indicated with the white dot in FIG. 3) after the waiting period has elapsed, the magnitude of the longitudinal magnetization is larger than zero. As a result, in the third data acquiring process (A3), the acquired data may have inappropriate data mixed therein in which the signal value of the blood is not sufficiently suppressed, and the quality of the generated image may be degraded.

As a method for preventing the image quality from being degraded by arrhythmia in this manner, a method called "arrhythmia removal method" is known, for example. According to this method, arrhythmia is detected on the basis of intervals between successive R-waves, and it is determined whether each piece of acquired data should be kept or discarded, on the basis of a result of the detection. In this situation, any piece of data that was acquired at the time when arrhythmia was detected is determined to be invalid data, which will not be used for the generation of an image. After that, to replace the invalid data, a new piece of data is re-acquired by extending the image taking period. For this reason, according to the arrhythmia removal method, the image taking period is extended as many times as arrhythmia occurs for the subject. For example, on the assumption that one heartbeat corresponds to one second, the image taking period is extended by three to four seconds every time arrhythmia is detected. During image taking processes performed on the heart, images are usually taken while the subject is holding his/her breath, in order to avoid imaging the heart during the respiratory movements thereof. However, when the image taking period is extended due to arrhythmia, it is difficult to perform the image taking process while the subject is holding his/her breath.

In view of the circumstances described above, the MRI apparatus 100 according to the first embodiment is configured to be able to obtain an image with excellent quality even when the cardiac cycle is disturbed by arrhythmia or the like, without the need to extend the image taking period to re-acquire the data.

More specifically, the MRI apparatus 100 is configured to execute a pulse sequence to acquire data from an image taking region, after applying a pre-pulse in synchronization with a predetermined ECG waveform of a subject. Further, the MRI apparatus 100 is configured to monitor recovery of longitudinal magnetization by acquiring data from a monitor region that is different from the image taking region, by using timing linked with the timing with which the pre-pulse is applied. Furthermore, the MRI apparatus 100 is configured to execute the pulse sequence on the basis of the signal value of the data from the monitor region.

In this configuration, the application of the pre-pulse and the data acquiring process from the image taking region are controlled on the basis of the signal value of the data acquired from the monitor region that is different from the image taking region. It is therefore possible to acquire appropriate data regardless of whether or not arrhythmia occurs. Accordingly, it is possible to obtain an image with excellent quality even when the cardiac cycle is disturbed by arrhythmia or the like, without the need to extend the image taking period to re-acquire the data. Further, it is possible to shorten the image taking period compared to situations where the arrhythmia removal method is implemented. In the present example, the data acquiring process denotes performing a series of processes from the time when the excitation-purpose RF pulse is applied to the time when the MR signal data is acquired. The pre-pulse denotes the RF pulse applied before a data acquiring process.

In the following sections, a configuration of the MRI apparatus 100 as described above will be explained further in detail, while a focus is placed on functions of the processing circuitries 13 and 15 illustrated in FIG. 1.

First, the processing circuitry 13 include an executing function 13*a*. The processing circuitry 13 is an example of the processing circuitry set forth in the claims.

The executing function 13*a* is configured to execute a pulse sequence to acquire data from an image taking region, after applying a pre-pulse in synchronization with a predetermined ECG waveform of the subject. Further, the executing function 13*a* is configured to acquire data from a monitor region that is different from the image taking region, by using timing linked with the timing with which the pre-pulse is applied.

In the first embodiment, the executing function 13*a* executes the pulse sequence to acquire the data from the image taking region, after applying the pre-pulse that changes longitudinal magnetization of a nuclear spin into a negative value, in synchronization with a predetermined cardiac phase of the subject. Further, every time the predetermined ECG waveform occurs, the executing function 13*a* acquires the data from the monitor region which is different from the image taking region and to which a pre-pulse is applied at the same time as the pre-pulse is applied to the image taking region.

In this situation, as a method for acquiring the data from the image taking region, any of various types of methods may be used. For example, it is possible to use a Fast Asymmetric Spin Echo (FASE) method, a Steady State Free Precession (SSFP) method, a Fast Field Echo (FFE) method, a Fast Spin Echo (FSE) method, or the like.

More specifically, the executing function 13*a* executes the abovementioned pulse sequence by driving the gradient power source 3, the transmission circuitry 5, and the reception circuitry 7, on the basis of sequence execution data output from the processing circuitry 15.

For example, the executing function 13*a* executes a pulse sequence to take a T2-weighted image of the heart in synchronization with R-waves. T2-weighted images are excellent in rendering infarction or inflammatory edema. In that situation, for example, the executing function 13*a* suppresses the signal value of the blood in the heart chambers, by executing a pulse sequence to acquire data from the image taking region at the time when the longitudinal magnetization of the blood has recovered up to a level close to zero, after applying a BB pulse to the blood flowing into the image taking region.

In this situation, for example, the executing function 13*a* simultaneously applies a BB pulse to an upstream part of the blood flowing into the image taking region and to a range including a monitor region set in a position different from that of the image taking region. For example, the executing function 13*a* applies the BB pulse while the regions are in a non-selected state. Applying the BB pulse while the regions are in a non-selected state denotes applying the BB pulse without applying a slice gradient magnetic field. As a result, the BB pulse is applied to the entirety of the range of which the MRI apparatus 100 is capable of taking an image. As the BB pulse, for example, an RF pulse that inverts the longitudinal magnetization of the nuclear spin by 180 degrees is used.

After that, the executing function 13*a* executes the pulse sequence in synchronization with an R-wave, by detecting a trigger signal output from the ECG circuitry 17 and executing the pulse sequence at the point in time when the trigger signal is detected. For example, the executing function 13*a* acquires data from the monitor region, every time an R-wave is detected by the ECG circuitry 17.

Figure 4:
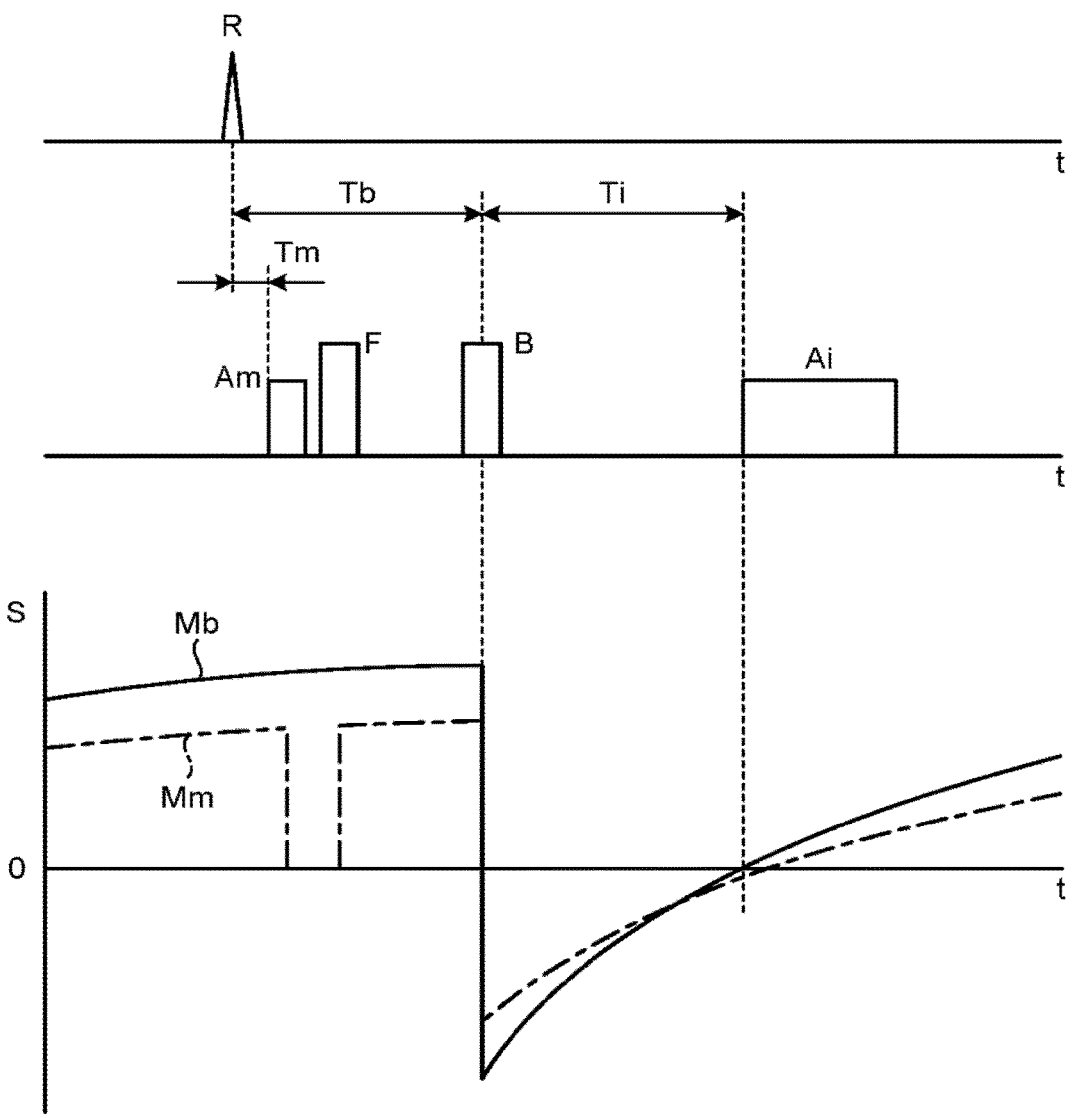
FIG. 4 is a time chart illustrating an example of a data acquiring process realized by an executing function according to the first embodiment.

FIG. 4 is a time chart illustrating an example of the data acquiring process realized by the executing function 13*a* according to the first embodiment. In the present example, the diagram in the top section of FIG. 4 illustrates the timing with which an R-wave is detected. In the diagram, the horizontal axis t expresses time. Further, the reference character "R" indicates the time at which the R-wave is detected.

Further, the diagram in the middle section of FIG. 4 illustrates the timing with which the application of a pre-pulse and the data acquiring process are performed. In the diagram, the horizontal axis t expresses time, which is aligned with the time in the diagram in the top section. The reference characters "Am" indicates the timing with which data is acquired from the monitor region. The reference character "F" indicates the timing with which a Flip Back (FB) pulse is applied. In the present example, the FB pulse denotes an RF pulse used for bringing the nuclear spin back into a longitudinal magnetization state, the nuclear spin being in a transverse magnetization state due to the excitation-purpose RF pulse applied when the data is acquired from the monitor region. The reference character "B" indicates the timing with which a BB pulse is applied. The reference characters "Ai" indicates the timing with which data is acquired from the image taking region.

The chart in the bottom section of FIG. 4 illustrates fluctuations of the signal values corresponding to the longitudinal magnetization of the blood and to the longitudinal magnetization of a tissue included in the monitor region. In the chart, the horizontal axis t expresses time, which is aligned with the time in the top and the middle sections. The vertical axis S expresses the signal value. The curve Mb illustrates the fluctuation of the signal value corresponding to the longitudinal magnetization of the blood. The curve Mm illustrates the fluctuation of the signal value corresponding to the longitudinal magnetization of the tissue included in the monitor region.

For example, as illustrated in FIG. 4, the executing function 13a executes the pulse sequence in which the BB pulse (B) is applied at the point in time when a predetermined time period Tb has elapsed since the R-wave is detected, and subsequently the data acquiring process (Ai) from the image taking region is started at the point in time when a waiting period Ti has elapsed.

In this situation, for example, the predetermined time period Tb is set with a fixed length of time. Further, the waiting time period Ti is set with a time period it takes for the longitudinal magnetization of the blood to recover and reach a level close to zero after being inverted by the BB pulse (B). The waiting time period Ti is a certain length of time determined on the basis of a longitudinal relaxation time period (which may be referred to as "T1") unique to blood, or the like.

Further, for example, as illustrated in FIG. 4, the executing function 13a performs a data acquiring process (Am) from the monitor region at the point in time when a predetermined time period Tm has elapsed since the point in time when the R-wave is detected. In the present example, the predetermined time period Tm is set with a fixed length of time. The time period Tm is set with a time period that is sufficiently shorter than the time period Tb, so that the data acquiring process (Am) from the monitor region and the application of the FB pulse (F) are finished before the application of the BB pulse (B).

Further, depending on the state of the subject, for example, R-waves may occur successively with a short interval therebetween, as observed in bigeminy. To cope with this situation, when a plurality of R-waves occur successively in a predetermined time period, the executing function 13a exercises control so that only the first R-wave occurring during the time period is adopted. For example, the executing function 13a performs the data acquiring process (Am) from the monitor region at the point in time when the time period Tm has elapsed since the point in time when the R-wave is detected. During the time period from the point in time when the data acquiring process (Am) is performed to the time when the data acquiring process (Am) and the application of the FB pulse (F) are completed, the executing function 13a exercises control so that neither a data acquiring process (Am) nor the application of an FB pulse (F) is performed even if the next R-wave occurs.

Further, the executing function 13a applies the FB pulse (F) to the monitor region, immediately after the data acquiring process (Am) from the monitor region is performed. For example, when having applied a 90°-pulse as the excitation-purpose RF pulse, the executing function 13a applies a −90°-pulse as the FB pulse. As a result, the nuclear spin in the transverse magnetization state due to the excitation-purpose RF pulse applied for acquiring the data from the monitor region is brought back into a longitudinal magnetization state. After that, the nuclear spin that has been brought back to the longitudinal magnetization state gradually recovers according to the longitudinal relaxation time period of the tissue included in the monitor region. As a result, it is possible to treat the signal value S in the monitor region as if recovering, as a whole, on a longitudinal relaxation curve that is substantially the same as the longitudinal relaxation curve observed before being affected by the RF pulse used in the data acquiring process, although there is a slight change due to an influence of the FB pulse. It means that the signal value S recovers according to the longitudinal relaxation time period of the tissue included in the monitor region.

Further, the longitudinal magnetization of the blood and the longitudinal magnetization of the tissue included in the monitor region are, for example, inverted into negative values at the same time as the BB pulse (B) is applied, as indicated by the curves Mb and Mm. After that, the signal values each recover gradually as time elapses. The longitudinal magnetization of the blood and the longitudinal magnetization of the tissue included in the monitor region both recover while exhibiting similar transitions until a next BB pulse is applied, although the speed of the recovery is different from each other. Accordingly, by monitoring the fluctuation of the signal value of the data acquired from the monitor region, it is possible to understand, as a result, the degree of recovery of the longitudinal magnetization of the blood.

Returning to the description of FIG. 1, the processing circuitry 15 includes a setting function 15a, a monitoring function 15b, and a controlling function 15c. The processing circuitry 15 is an example of the processing circuitry set forth in the claims.

The setting function 15a is configured to receive, from the operator, an operation to designate a range within an image of the subject displayed on the display 10 and to set a monitor region on the basis of the received range.

More specifically, the setting function 15a displays, on the display 10, a Graphical User Interface (GUI) used for receiving an operation to select a pulse sequence to be used in an image taking process and an operation to input various types of parameters related to the selected pulse sequence. After that, the setting function 15a generates sequence execution data used for executing the selected pulse sequence on the basis of input values of the various types of parameters received via the GUI and further outputs the generated sequence execution data to the processing circuitry 13.

For example, the setting function 15a displays an image of the subject on the GUI as a position determining image and receives, from the operator, an operation to designate a range serving as an image taking region and a range serving as a monitor region, within the position determining image. Further, the setting function 15a receives, from the operator, an operation to designate a range serving as an FB pulse application region within the position determining image. After that, the setting function 15a generates sequence execution data used for acquiring data from the image taking region and from the monitor region, on the basis of the designated ranges.

Figure 5:
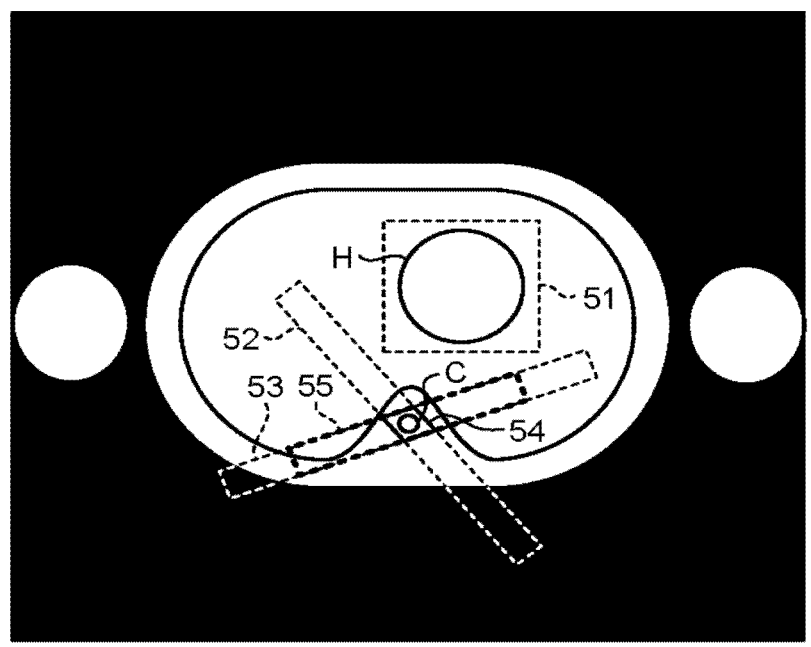
FIGS. 5 and 6 are drawings illustrating examples of an image taking region setting process and a monitor region setting process realized by a setting function according to the first embodiment.
Figure 6:
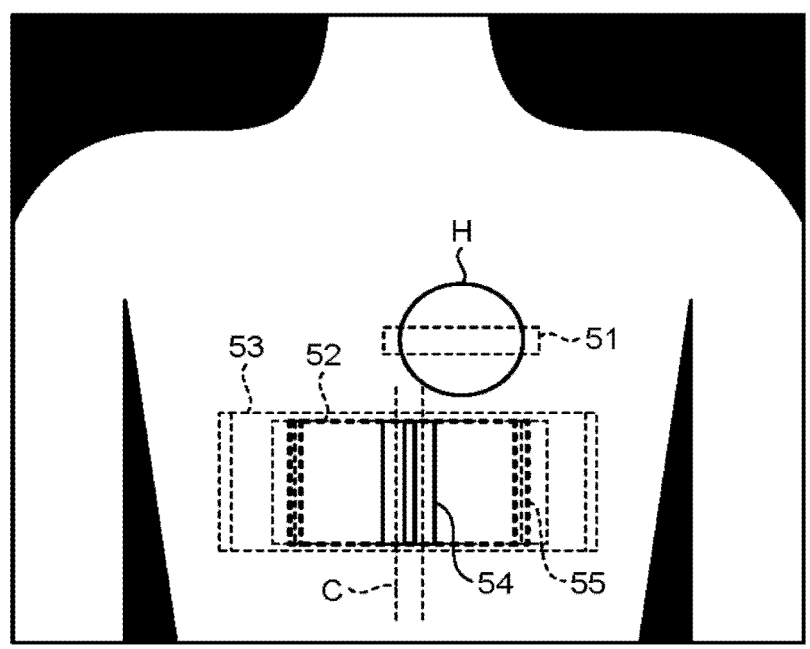

FIGS. 5 and 6 are drawings illustrating examples of the image taking region setting process and the monitor region setting process realized by the setting function 15a according to the first embodiment. For example, as illustrated in FIG. 5, the setting function 15a displays an axial image of the subject on the GUI, as a first position determining image. Further, for example, as illustrated in FIG. 6, the setting function 15a displays a coronal image of the subject on the GUI, as a second position determining image.

After that, the setting function 15a receives, from the operator, an operation to designate a range 51 serving as an image taking region, within each of the axial and the coronal images. For example, to take a T2-weighted image of the heart, the image taking region is set so as to include a myocardium of the subject ("H" in FIGS. 5 and 6).

In this situation, the number of ranges each set as an image taking region may be one or may be two or more. When one range is set, the setting function 15a generates sequence execution data so as to take one slice image. When two or more ranges are set, the setting function 15a generates sequence execution data so as to take multi-slice images corresponding to the ranges.

Further, the setting function 15a receives, from the operator, an operation to designate a range serving as a monitor region, within each of the axial and the coronal images. For example, the setting function 15a receives an operation to set two ranges 52 and 53 within each of the axial and the coronal images and further sets an intersection range 54 where the range 52 and the range 53 intersect each other, as a monitor region. For example, the monitor region is set so as to include cerebrospinal fluid (CSF) ("C" in FIGS. 5 and 6) that is in the spine of the subject.

Further, for example, the setting function 15a generates sequence execution data to execute a pulse sequence according to a Spin Echo (SE) method by which an excitation-purpose RF pulse (a 90°-pulse) is applied to a region corresponding to the range 52 and a re-focus pulse (a 180°-pulse) is applied to a region corresponding to the range 53. As a result, by implementing the SE method, data is acquired from the monitor region that is set as the range where the range 52 and the range 53 intersect each other.

When the method for setting the monitor region as described above is used, it is desirable to set the ranges 52 and 53 so as not to overlap the range 51 serving as the image taking region. The reason is that, when any of the application regions overlaps the image taking region, artifact may occur in the image in relation to the recovery of the longitudinal magnetization.

Further, the method for setting the monitor region implemented by the setting function 15a is not limited to the example explained above. For instance, the setting function 15a may automatically set a monitor region, instead of receiving the designations of the ranges from the operator. In that situation, for example, the storage circuitry 11 is arranged to store therein a model image defining a positional relationship between an abdomen region of a subject having a typical physique and a monitor region. Further, the setting function 15a reads the model image from the storage circuitry 11 and further sets a monitor region in the position determining image by matching the read model image with the position determining image of the subject.

Further, the setting function 15a receives, from the operator, an operation to set an FB pulse application region. For example, similarly to the operation to set the ranges 52 and 53 described above, the setting function 15a receives an operation to set a range 55 within each of the axial and the coronal images. In that situation, the setting function 15a receives the operation to set the range 55 so as to overlap the intersection range 54 serving as the monitor region. Further, the setting function 15a sets the range 55 that has been set as the FB pulse application region. Also, similarly to the ranges 52 and 53, it is desirable to set the range 55 serving as the FB pulse application region so as not to overlap the range 51 serving as the image taking region, in order to prevent artifact from occurring in the image.

The monitoring function 15b is configured to monitor the recovery of the longitudinal magnetization, by acquiring the data from the monitor region that is different from the image taking region, by using timing linked with the timing with which the pre-pulse is applied.

In the first embodiment, the monitoring function 15b obtains a signal value of the data acquired from the monitor region which is different from the image taking region and to which the pre-pulse is applied. For example, every time data is acquired from the monitor region, the monitoring function 15b obtains the signal value of the acquired data.

More specifically, every time data is acquired from the monitor region by the executing function 13a, the monitoring function 15b reads the acquired data from the storage circuitry 11. Further, the monitoring function 15b obtains the signal value of the data read from the storage circuitry 11.

The controlling function 15c is configured to control the execution of the pulse sequence, on the basis of the signal value of the data from the monitor region.

In the first embodiment, the controlling function 15c controls the execution of the pulse sequence on the basis of the signal value of the data from the monitor region obtained by the monitoring function 15b. For example, when the signal value obtained by the monitoring function 15b is equal to or larger than a predetermined threshold value, the controlling function 15c exercises control so that the pulse sequence is executed in the upcoming predetermined cardiac phase. When the obtained signal value is smaller than the predetermined threshold value, the controlling function 15c exercises control so that the pulse sequence is not executed in the upcoming predetermined cardiac phase.

More specifically, every time a signal value is obtained by the monitoring function 15b, the controlling function 15c compares the obtained signal value with the predetermined threshold value. Further, when the signal value is equal to or larger than the threshold value, the controlling function 15c controls the executing function 13a so as to execute the pulse sequence at the upcoming R-wave. On the contrary, when the signal value is smaller than the threshold value, the controlling function 15c controls the executing function 13a so as not to execute the pulse sequence at the upcoming R-wave.

Figure 7:
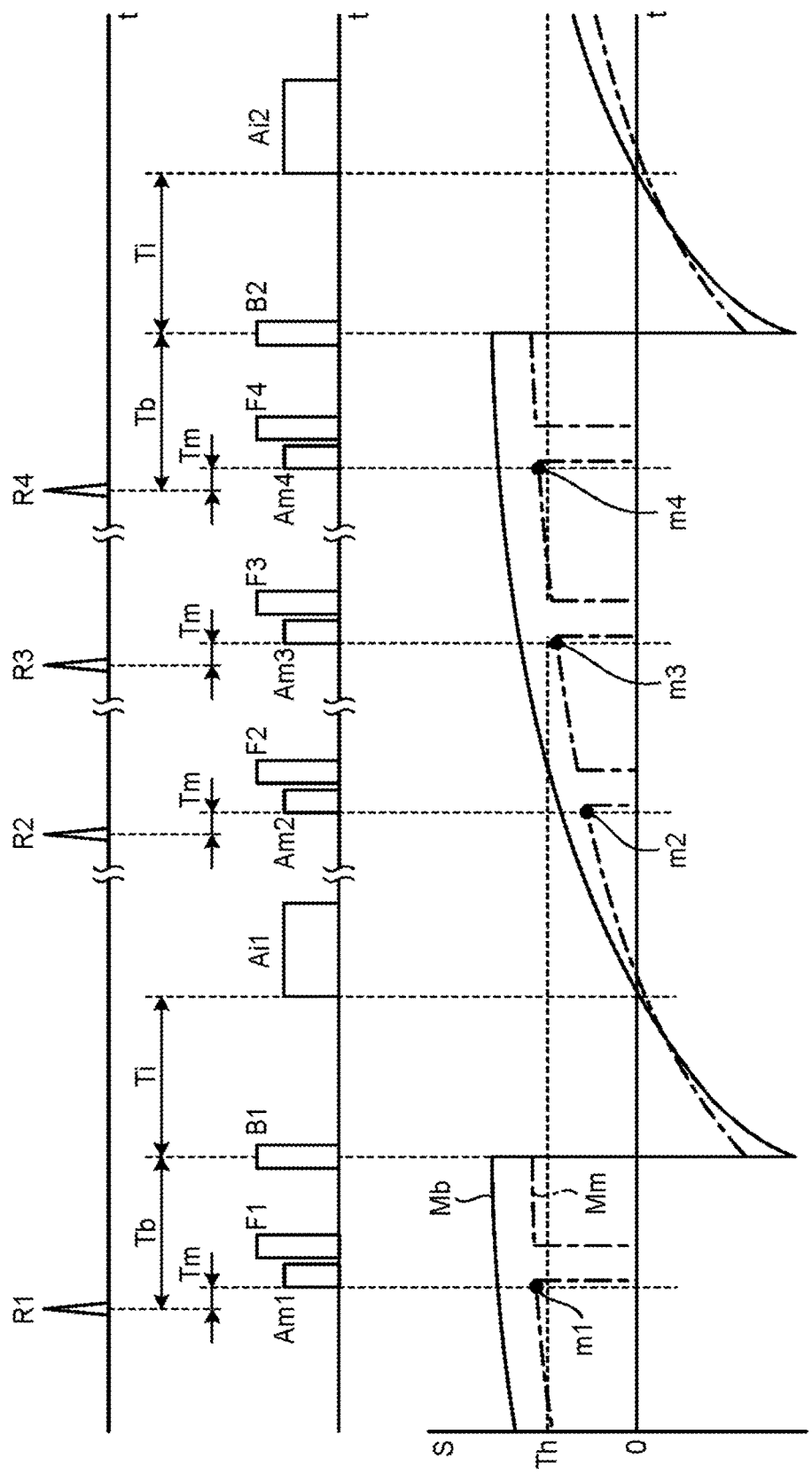
FIG. 7 is a time chart illustrating an example of control realized by a controlling function according to the first embodiment.

FIG. 7 is a time chart illustrating an example of the control realized by the controlling function 15c according to the first embodiment. In the present example, the diagram in the top section of FIG. 7 illustrates the timing with which R-waves are detected, similarly to the diagram in the top section of FIG. 4. Further, the diagram in the middle section of FIG. 7 illustrates the timing with which the applications of a pre-pulse and the data acquiring processes are performed, similarly to the diagram in the middle section of FIG. 4. Further, the chart in the bottom section of FIG. 7 illustrates fluctuations of the signal values corresponding to the longitudinal magnetization of the blood and to the longitudinal magnetization of the tissue included in the monitor region, similarly to the chart in the bottom section of FIG. 4.

For example, as illustrated in FIG. 7, when the first R-wave (R1) is detected, the executing function 13a performs a data acquiring process (Am1) from the monitor region at the point in time when the time period Tm has elapsed. Immediately after that, an FB pulse (F1) is applied to the monitor region. After that, the controlling function 15c compares the signal value of the data acquired from the monitor region with a threshold value Th. In this situation, for example, when the signal value is equal to or larger than the threshold value Th as indicated by the black dot m1 in FIG. 7, the controlling function 15c controls the executing function 13a so as to apply a BB pulse (B1) at the time when the time period Tb has elapsed since the first R-wave (R1). As a result, the application of the BB pulse (B1) and the data acquiring process (Ai1) from the image taking region are performed in synchronization with the first R-wave (R1).

Further, as illustrated in FIG. 7, when the second R-wave (R2) is detected, the executing function 13a performs a data acquiring process (Am2) from the monitor region at the point in time when the time period Tm has elapsed, similarly to the situation with the first R-wave (R1). Immediately after that, an FB pulse (F2) is applied to the monitor region. After that, the controlling function 15c compares the signal value of the data acquired from the monitor region with the threshold value Th. In this situation, for example, when the signal value is smaller than the threshold value as indicated by the black dot m2 in FIG. 7, the controlling function 15c controls the executing function 13a so as not to apply a BB pulse. As a result, neither the application of a BB pulse nor a data acquiring process from the image taking region is performed at the second R-wave (R2).

Further, as illustrated in FIG. 7, when the third R-wave (R3) is detected, the executing function 13a performs a data acquiring process (Am3) from the monitor region at the point in time when the time period Tm has elapsed, similarly to the situations with the first and the second R-waves (R1 and R2). Immediately after that, an FB pulse (F3) is applied to the monitor region. After that, the controlling function 15c compares the signal value of the data acquired from the monitor region with the threshold value Th. In this situation, for example, when the signal value is smaller than the threshold value as indicated by the black dot m3 in FIG. 7, the controlling function 15c controls the executing function 13a so as not to apply a BB pulse. As a result, neither the application of a BB pulse nor a data acquiring process from the image taking region is performed at the third R-wave (R3).

Further, as illustrated in FIG. 7, when the fourth R-wave (R4) is detected, the executing function 13a performs a data acquiring process (Am4) from the monitor region at the point in time when the time period Tm has elapsed. Immediately after that, an FB pulse (F4) is applied to the monitor region. After that, the controlling function 15c compares the signal value of the data acquired from the monitor region with the threshold value Th. In this situation, for example, when the signal value is equal to or larger than the threshold value Th as indicated by the black dot m4 in FIG. 7, the controlling function 15c controls the executing function 13a so as to apply a BB pulse (B2) at the time when the time period Tb has elapsed since the fourth R-wave (R4). As a result, the application of the BB pulse (B2) and the data acquiring process (Ai2) from the image taking region are performed in synchronization with the fourth R-wave (R4).

As explained above, the controlling function 15c controls the execution of the pulse sequence on the basis of the signal value of the data from the monitor region that is different from the image taking region. In other words, the controlling function 15c understands the degree of recovery of the longitudinal magnetization of the blood by monitoring the fluctuation of the signal value of the data acquired from the monitor region, and further determines whether or not the application of a BB pulse and a data acquiring process from the image taking region should be performed at the upcoming R-wave in accordance with the degree of recovery.

Figure 8:
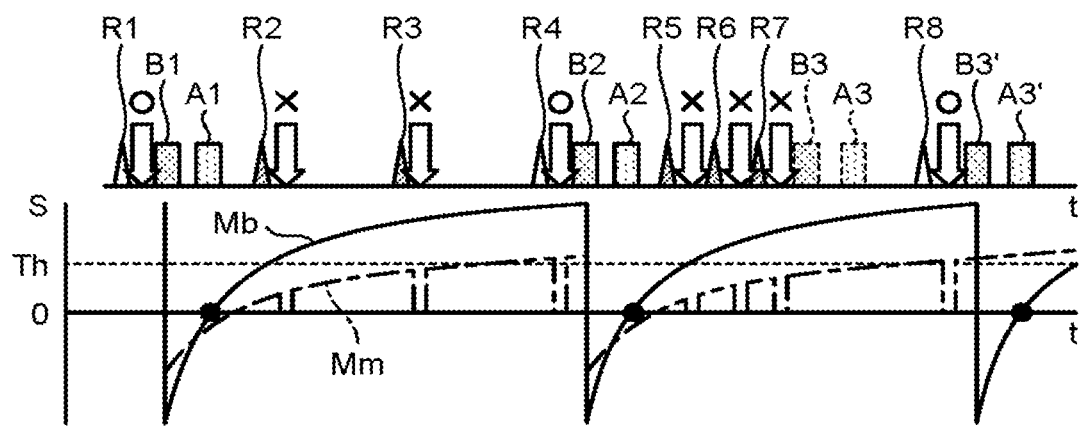
FIG. 8 is a time chart illustrating an example of a result of the control realized by the controlling function according to the first embodiment.
Figure 9:
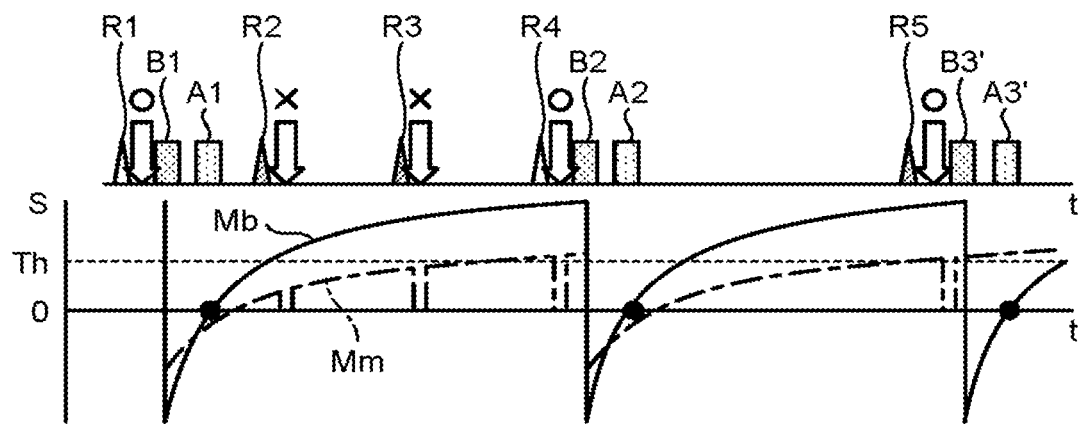
FIG. 9 is a time chart illustrating another example of the result of the control realized by the controlling function according to the first embodiment.

FIG. 8 is a time chart illustrating an example of a result of the control realized by the controlling function 15c according to the first embodiment. FIG. 9 is a time chart illustrating another example of the result of the control realized by the controlling function 15c according to the first embodiment. FIG. 8 illustrates the time chart of a situation where the intervals of the R-waves started to be shorter due to arrhythmia during the period of time. FIG. 9 illustrates the example in which the intervals of the R-waves started to be longer due to arrhythmia during the period of time.

In the present example, the diagrams in the top sections of FIGS. 8 and 9 illustrate the timing of R-waves, pre-pulses, and data acquiring processes, similarly to the diagrams in the top sections of FIGS. 2 and 3. In FIGS. 8 and 9, the data acquiring processes from the monitor region and the applications of the FB pulse performed by the executing function 13a are omitted from the drawings. Further, the downward arrows in FIGS. 8 and 9 each illustrate a time at which the controlling function 15c determines whether or not the pulse sequence should be executed. In the present example, the symbol "O" above the arrows indicates that the controlling function 15c determines that the pulse sequence should be executed. On the contrary, the symbol "X" indicates that the controlling function 15c determines that the pulse sequence should not be executed. Further, the charts in the bottom sections of FIGS. 8 and 9 illustrate fluctuations of the signal values corresponding to the longitudinal magnetization of the blood, similarly to the charts in the bottom sections of FIGS. 2 and 3.

Further, similarly to the example in FIG. 3, FIG. 8 illustrates the example in which the intervals of the R-waves are substantially regular during the time period from the first R-wave to the fifth R-wave (R1 to R5), and the intervals of the R-waves become shorter due to arrhythmia during the time period from the fifth R-wave to the seventh R-wave (R5 to R7). In that situation, for example, if the application of a BB pulse and a data acquiring process from the image taking region were performed with the fixed frequency of once every three heartbeats as illustrated in FIG. 3, the application of a BB pulse and a data acquiring process from the image taking region would be performed at each of the first, the fourth, and the seventh R-waves (R1, R4, and R7). In that situation, however, as illustrated in FIG. 3, the data acquired in the third data acquiring process (A3), which would be performed after the intervals of the R-waves become shorter due to arrhythmia, would have inappropriate data mixed therein in which the signal value of the blood is not sufficiently suppressed.

In contrast, the controlling function 15c described above determines whether or not the pulse sequence including the application of a BB pulse and a data acquiring process from the image taking region should be executed, on the basis of the signal value of the data from the monitor region, instead of performing the application of a BB pulse and a data acquiring process from the image taking region with the fixed frequency of once every three heartbeats. Accordingly, as illustrated in FIG. 8, the third application of a BB pulse (B3') and the third data acquiring process from the image taking region (A3') are not performed at the seventh R-wave (R7) at which the signal value of the data from the monitor region is smaller than the threshold value, but are instead performed at the eighth R-wave (R8), for example, at which the signal value of the data from the monitor region is equal to or larger than the threshold value.

In contrast, FIG. 9 illustrates the example in which the intervals of the R-waves are substantially regular during the time period from the first R-wave to the fourth R-wave (R1 to R4), and the interval of the R-waves becomes longer due to arrhythmia during the time period from the fourth R-wave to the fifth R-wave (R4 to R5). In that situation, if the application of a BB pulse and a data acquiring process from the image taking region were performed with the fixed frequency of once every three heartbeats, the application of a BB pulse and a data acquiring process from the image taking region would be performed at each of the first and the fourth R-waves (R1 and R4), and neither the application of a BB pulse nor a data acquiring process from the image taking region would be performed at the fifth R-wave (R5).

In contrast, the controlling function 15c described above determines whether or not the pulse sequence including the application of a BB pulse and a data acquiring process from the image taking region should be executed, on the basis of the signal value of the data from the monitor region, instead of performing the application of a BB pulse and a data acquiring process from the image taking region with the fixed frequency of once every three heartbeats. Accordingly, as illustrated in FIG. 9, the third application of a BB pulse (B3') and the third data acquiring process from the image taking region (A3') are performed, when the signal value of the data from the monitor region acquired at the fifth R-wave (R5) is equal to or larger than the threshold value.

As explained above, the controlling function 15c is configured to control the applications of the BB pulse and the data acquiring processes from the image taking region, on the basis of the signal value of the data from the monitor region, instead of the intervals of the R-waves. Accordingly, it is possible to acquire the data from the image taking region with appropriate timing, even when the intervals of the R-waves become shorter and even when the intervals of the R-waves become longer due to arrhythmia. In other words, it is possible to acquire appropriate data regardless of whether or not arrhythmia occurs.

For the control exercised by the controlling function 15c described above, it is desirable to set the monitor region so as to include a tissue of which the longitudinal relaxation time period is equal to or longer than the longitudinal relaxation time period of the tissue of which the signal value is suppressed by the pre-pulse. The reason is that it is easier to understand the degree of recovery of the longitudinal magnetization by comparing the signal value with the threshold value, because the longer the longitudinal relaxation time period is, the longer it takes for the fluctuation of the longitudinal magnetization to become stable.

For example, when the tissue of which the signal value is suppressed is blood, the monitor region is set so as to include cerebrospinal fluid (CSF) that is in the spine of the subject, as mentioned above. The reason is that it is possible to detect the signal value in a stable manner, because cerebrospinal fluid has a composition close to that of water and therefore has a high signal value and because cerebrospinal fluid moves more slowly in the body of the subject than blood or the like does.

The relevant constituent elements of the MRI apparatus 100 have thus been explained. In the present example, for instance, the processing functions included in the processing circuitries 12 to 15 described above are stored in the storage circuitry 11 in the form of computer programs (hereinafter, "programs") that are executable by a computer. The processing circuitries 12 to 15 are configured to realize the processing functions corresponding to the programs by reading the programs from the storage circuitry 11 and executing the read programs. In other words, the processing circuitries 12 to 15 that have read the programs have the processing functions illustrated in FIG. 1.

Further, FIG. 1 illustrates the example in which the single processing circuitry 12 realizes the processing function of the couch controlling function 12a; the single processing circuitry 13 realizes the processing function of the executing function 13a; the single processing circuitry 14 realizes the processing function of the image generating function 14a; and the single processing circuitry 15 realizes the processing functions of the setting function 15a, the monitoring function 15b, and the controlling function 15c. However, possible embodiments are not limited to this example. For instance, each of the processing circuitries 12 to 15 may be structured by combining a plurality of independent processors together, so that the processing functions are realized as a result of the processors executing the programs. Further, the processing functions of the processing circuitries 12 to 15 may be realized as being distributed to or integrated into one or more processing circuitries, as appropriate.

Further, the term "processor" used in the explanation above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, it is also acceptable to configure the programs to be directly incorporated into the circuit of the processor, instead of having the programs saved in the storage circuitry 11. In that situation, the processor realizes the functions by reading the programs incorporated in the circuit and executing the read programs. Further, the processors according to the first embodiment do not necessarily have to be structured in such a manner that each of the processors corresponds to a single circuit, but may be structured in such a manner that a plurality of independent circuits are combined as one processor that the functions thereof are realized.

Figure 10:
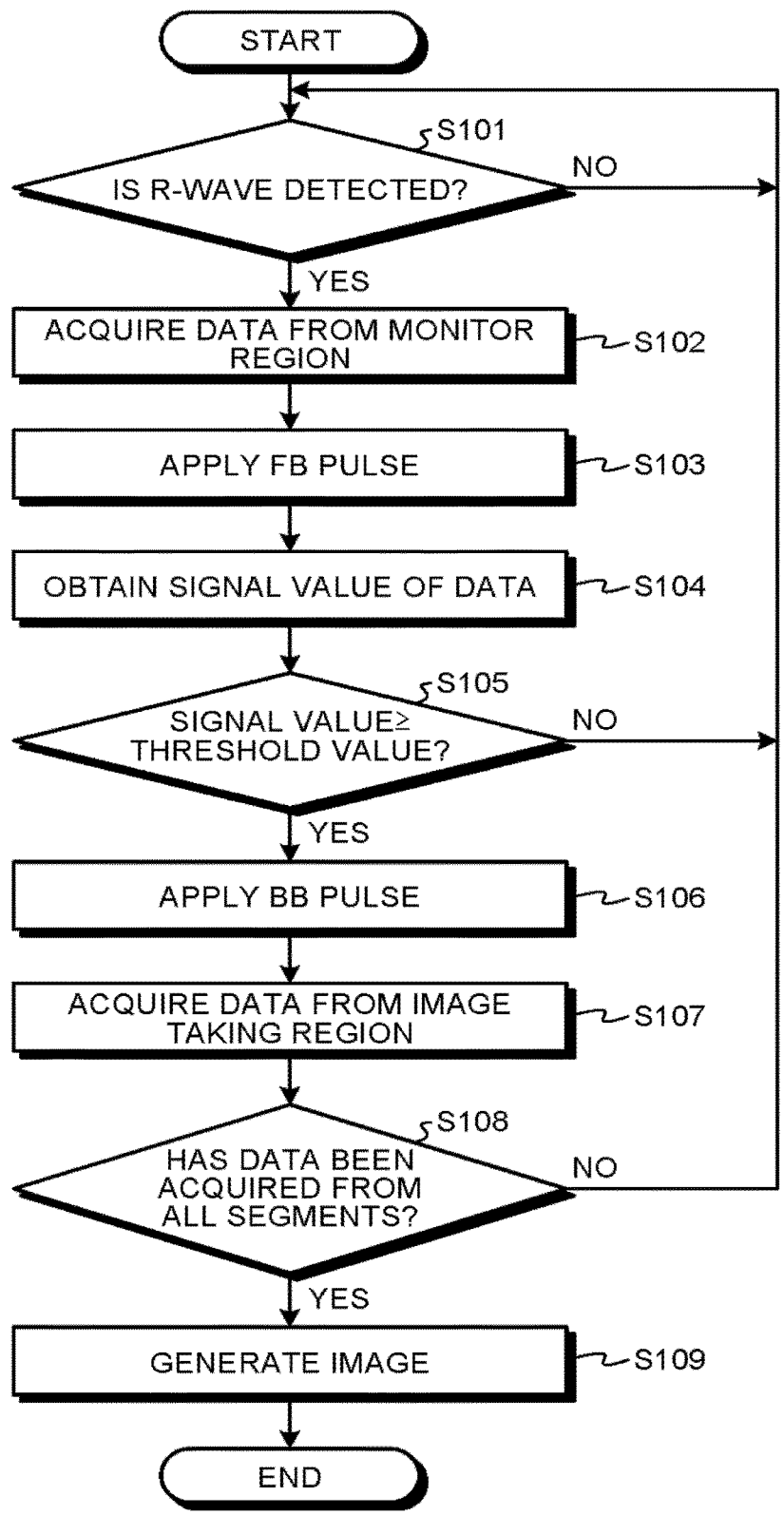
FIG. 10 is a flowchart illustrating a processing procedure according to an image taking method implemented by the MRI apparatus according to the first embodiment.

FIG. 10 is a flowchart illustrating a processing procedure according to an image taking method implemented by the MRI apparatus 100 according to the first embodiment. For example, as illustrated in FIG. 10, in the MRI apparatus 100, when the ECG circuitry 17 detects an R-wave (step S101: Yes), the executing function 13a acquires data from the monitor region (step S102). Immediately after that, the executing function 13a applies an FB pulse to the monitor region (step S103). In this situation, the executing function 13a stands by without acquiring any data from the monitor region until another R-wave is detected (step S101: No).

Further, when the executing function 13a has acquired the data from the monitor region, the monitoring function 15b obtains the signal value of the data from the monitor region (step S104). After that, when the monitoring function 15b has obtained the signal value of the data from the monitor region, the controlling function 15c compares the signal value obtained by the monitoring function 15b with the predetermined threshold value (step S105).

In this situation, when the signal value is equal to or larger than the threshold value (step S105: Yes), the controlling function 15c controls the executing function 13a so as to acquire data from the image taking region after applying a BB pulse (steps S106 and S107). On the contrary, when the signal value is smaller than the threshold value, the controlling function 15c controls the executing function 13a so as not to perform the application of a BB pulse and a data acquiring process from the image taking region and stands by until the next time when a signal value of the data from the monitor region is obtained (step S105: No).

In this manner, the controlling function 15c controls the executing function 13a so as to repeatedly perform a data acquiring process from the image taking region until the data is acquired from all the segments (step S108: No). When the controlling function 15c has acquired the data from all the segments (step S108: Yes), the image generating function 14a generates an image on the basis of the acquired data (step S109).

In the present example, steps S101 through S103 are steps realized as a result of the processing circuitry 13 invoking the predetermined program corresponding to the executing function 13a from the storage circuitry 11 and executing the invoked program. Step S104 is a step realized as a result of the processing circuitry 15 invoking the predetermined program corresponding to the monitoring function 15b from the storage circuitry 11 and executing the invoked program. Step S105 through S108 are steps realized as a result of the processing circuitry 15 invoking the predetermined program corresponding to the controlling function 15c from the storage circuitry 11 and executing the invoked program. Further, step S109 is a step realized as a result of the processing circuitry 14 invoking the predetermined program corresponding to the image generating function 14a from the storage circuitry 11 and executing the invoked program.

As explained above, in the first embodiment, the applications of the BB pulse and the data acquiring processes from the image taking region are controlled on the basis of the signal values of the data acquired from the monitor region that is different from the image taking region. Accordingly, it is possible to acquire appropriate data regardless of whether or not arrhythmia occurs. Consequently, according to the first embodiment, it is possible to obtain an image having excellent quality even when the cardiac cycle is disturbed by arrhythmia or the like, without the need to extend the image taking time period to re-acquire the data. Further, compared to situations where the arrhythmia removal method is implemented, it is possible to shorten the image taking time period.

The MRI apparatus 100 according to the first embodiment described above may be embodied as being modified as appropriate in accordance with various situations. Thus, in the following sections, other embodiments of the MRI apparatus 100 will be explained. The configuration of the MRI apparatus 100 described below is the same as the configuration illustrated in in FIG. 1. Thus, in the following sections, the explanation of some of the features that are the same as those in the first embodiment will be omitted. A focus will be placed on the features that are different from those in the first embodiment.

Second Embodiment

For example, in the embodiment described above, the example is explained in which, as illustrated in FIG. 4, the time period Tb from the time when an R-wave is detected to the time when a BB pulse is applied is fixed; however, possible embodiments are not limited to this example. For instance, the intervals of the R-waves of the subject are considered to vary more or less, even if no arrhythmia occurs. Thus, in a second embodiment, an example will be explained in which the time period Tb is adjusted for each of the R-waves in accordance with the degree of recovery of the longitudinal magnetization.

In that situation, the controlling function 15c sets the time period from the time when a predetermined ECG waveform is detected to the time when a pre-pulse is applied, in accordance with how large the difference is between the signal value of the data from the monitor region obtained by the monitoring function 15b and a predetermined threshold value.

For example, when the signal value obtained by the monitoring function 15b exceeds the predetermined threshold value, the controlling function 15c calculates the difference between the signal value and the predetermined threshold value. Further, in accordance with how large the calculated difference is, the controlling function 15c sets the time period Tb from the point in time when the R-wave is detected to the time when a BB pulse is applied. In this situation, the controlling function 15c sets the time period Tb in such a manner that the magnitudes of the longitudinal magnetization of the blood at the points in time when a BB pulse is applied have a constant value.

Figure 11:
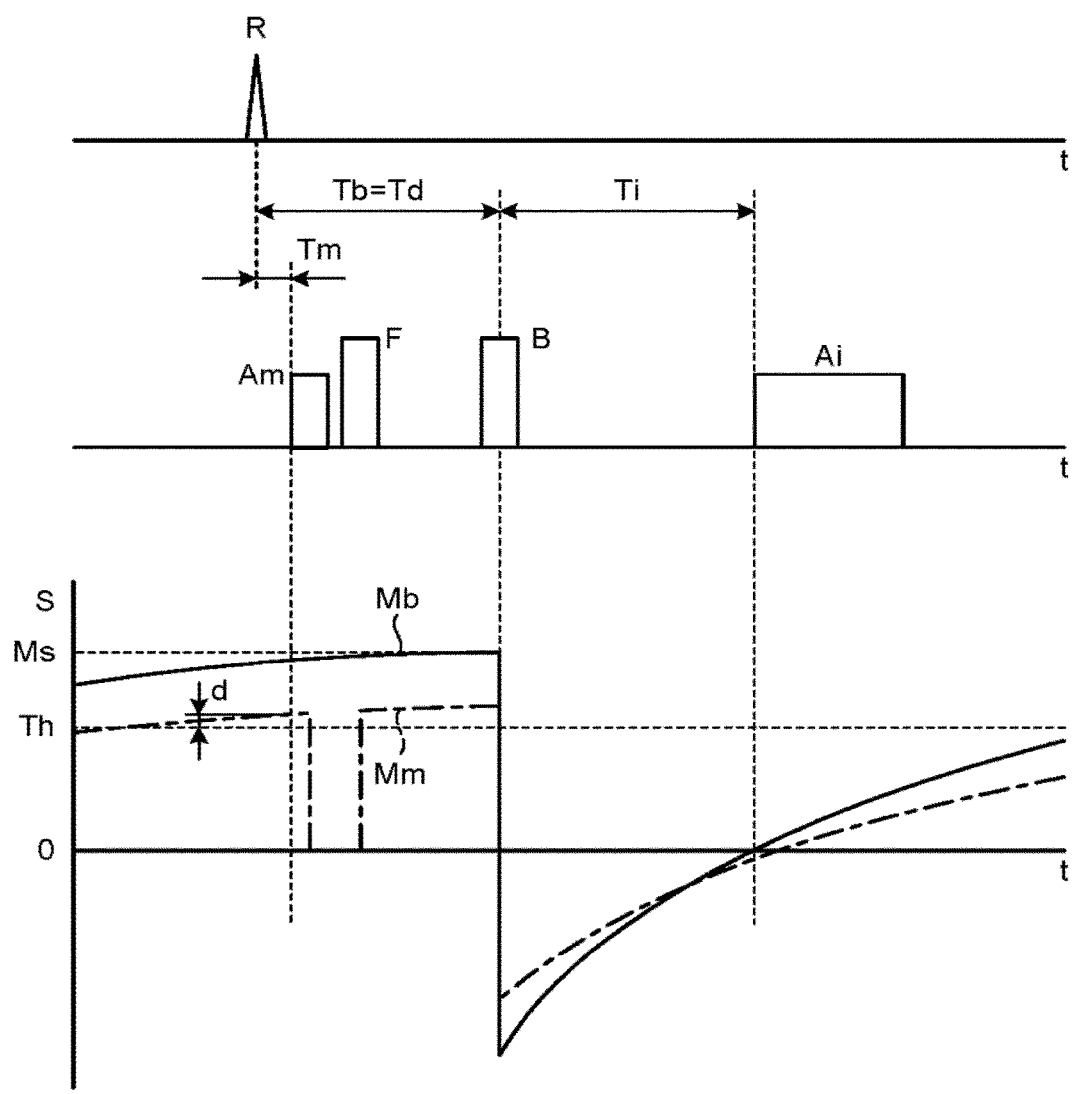
FIGS. 11 and 12 are time charts each illustrating an example of a data acquiring process performed by an MRI apparatus according to a second embodiment.
Figure 12:
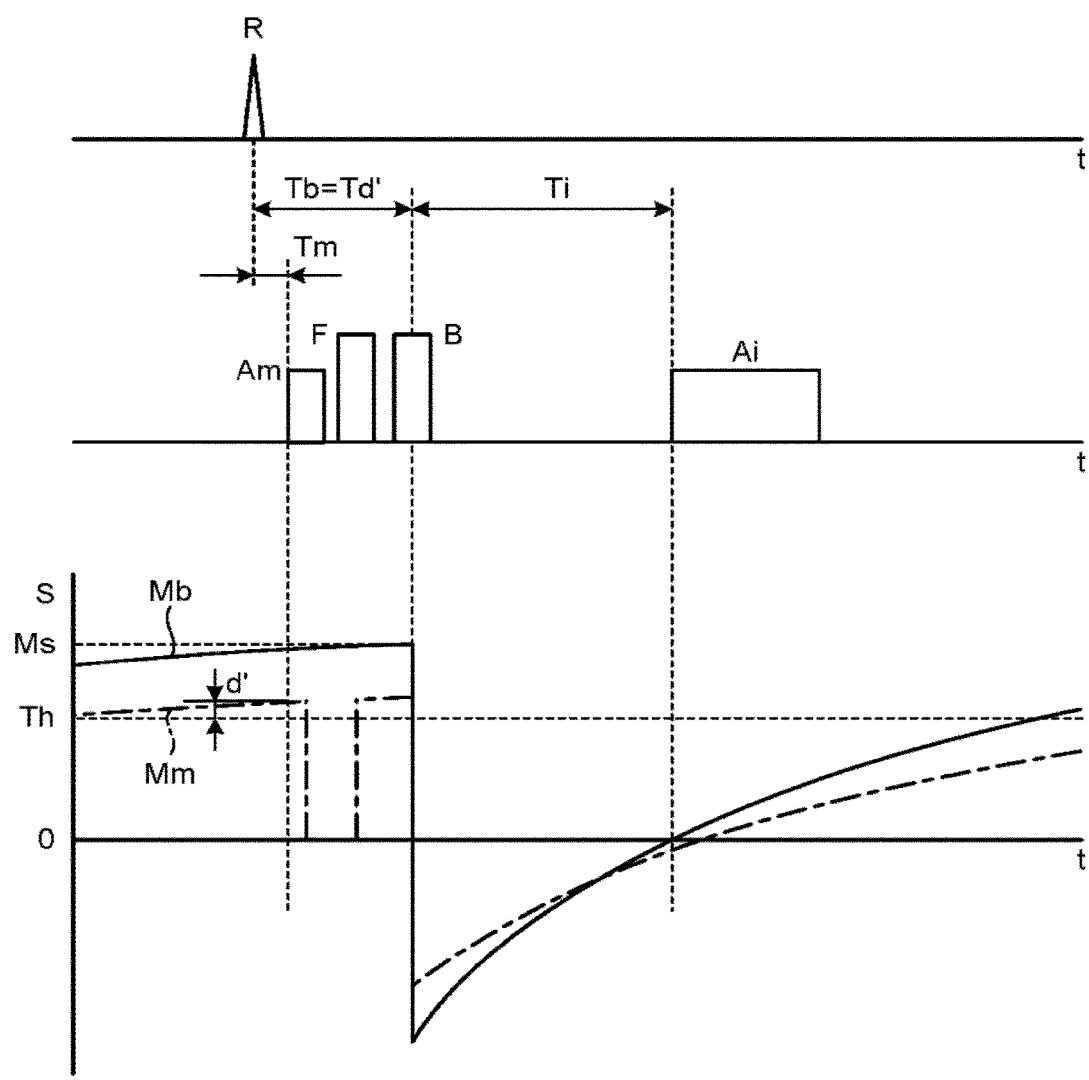

FIGS. 11 and 12 are time charts each illustrating an example of a data acquiring process performed by the MRI apparatus according to the second embodiment. For example, as illustrated in FIG. 11, let us assume that the difference between the signal value of the data from the monitor region and the threshold value Th is equal to d, at a certain R-wave. Further, in that situation, let us assume that the time period it takes for the signal value to reach a predetermined value Ms after the R-wave is detected is equal to Td. In that situation, the controlling function 15c sets the time period Tb so as to be equal to Td.

In contrast, for example, as illustrated in FIG. 12, let us assume that the difference between the signal value of the data from the monitor region and the threshold value Th is equal to d' at another R-wave. Further, in that situation, let us assume that the time period it takes for the signal value to reach the predetermined value Ms after the R-wave is detected is equal to Td'. In that situation, the controlling function 15c sets the time period Tb so as to be equal to Td'.

In this situation, as illustrated in FIG. 12, for example, when d' is larger than d illustrated in FIG. 11, it means that, at the point in time when the data is acquired from the monitor region, the longitudinal magnetization of the blood has recovered more than in the example in FIG. 11. Accordingly, in that situation, the time period Td' it takes for the signal value to reach the predetermined value Ms after the R-wave is detected is shorter than Td illustrated in FIG. 11. In other words, the time period Tb from the time when the R-wave is detected to the time when the BB pulse is applied is set so as to be shorter than the time period Tb illustrated in FIG. 11.

Conversely, for example, there may be a situation where d' is smaller than d illustrated in FIG. 11, contrary to the example in FIG. 12. In that situation, it means that, at the point in time when the data is acquired from the monitor region, the longitudinal magnetization of the blood has recovered less than in the example in FIG. 11. Accordingly, in that situation, the time period Td' it takes for the signal value to reach the predetermined value Ms after the R-wave is detected is longer than Td illustrated in FIG. 11. In other words, the time period Tb from the time when the R-wave is detected to the time when the BB pulse is applied is set so as to be longer than the time period Tb illustrated in FIG. 11.

As explained above, in the second embodiment, the time period from the time when the predetermined ECG waveform is detected to the time when a pre-pulse is applied is set in accordance with how large the difference is between the signal value of the data from the monitor region and the predetermined threshold value, for each of the occurrences of the predetermined ECG waveform. Consequently, according to the second embodiment, it is possible to arrange the signal values to be more uniform among the pieces of data and among the segments. It is therefore possible to further improve the quality of the generated image.

Third Embodiment

Further, for example, in the embodiment described above, the example is explained in which it is determined whether or not the pulse sequence should be executed, on the basis of the signal value of the data from the monitor region, for each of the R-waves; however, possible embodiments are not limited to this example. For instance, another arrangement is acceptable in which a sequence is executed so as to acquire data from the monitor region and from the image taking region after applying a pre-pulse in synchronization with an ECG waveform of the subject, and after the data acquiring process is performed at least once, it is determined whether the data acquired from the image taking region should be kept or discarded, on the basis of the signal value of the data acquired from the monitor region. In the following sections, an example with this arrangement will be explained as a third embodiment.

In that situation, the controlling function 15c controls the executing function 13a so as to execute a pulse sequence to acquire data from the monitor region and from the image taking region after applying a pre-pulse in synchronization with the ECG waveform of the subject. For example, the controlling function 15c executes the pulse sequence in synchronization with R-waves detected by the ECG circuitry 17. In this situation, for example, the controlling function 15c executes the pulse sequence once every three heartbeats.

Further, every time the pulse sequence is executed once, the controlling function 15c determines whether the data acquired from the image taking region should be kept or discarded, on the basis of the signal value of data acquired from the monitor region. For example, when the signal value of the data acquired from the monitor region is equal to or larger than a predetermined threshold value, the controlling function 15c determines the data acquired from the image taking region to be valid data that is to be used for the generation of an image. On the contrary, when the signal value of the data acquired from the monitor region is smaller than the predetermined threshold value, the controlling function 15c determines the data acquired from the image taking region to be invalid data that is not to be used for the generation of an image. After that, when the data acquired from the image taking region is determined to be invalid data, the controlling function 15c controls the executing function 13a so as to acquire the corresponding data again.

In this situation, the controlling function 15c may be configured to determine whether the data should be kept or discarded once every multiple executions (i.e., two or more times) of the pulse sequence, instead of determining whether the data should be kept or discarded every time the pulse sequence is executed. Further, the controlling function 15c may be configured so as to determine whether the data should be kept or discarded for pieces of data altogether, after the pulse sequence has been performed as many times as required by acquiring a certain amount of data necessary for the generation of an image.

As explained above, in the third embodiment, it is determined whether the data acquired from the image taking region should be kept or discarded on the basis of the signal value of the data acquired from the monitor region, after the data is acquired in synchronization with the ECG waveform of the subject. As a result, although it may be necessary to re-acquire some data, it is possible to acquire appropriate data on the basis of the signal values of the data acquired from the monitor region.

Fourth Embodiment

Further, for example, in the embodiment described above, the example is explained in which the signal value in the monitor region as a whole is arranged to recover according to the longitudinal relaxation time period, by changing the state of the nuclear spin back into a longitudinal magnetization state with the use of the FB pulse; however, possible embodiments are not limited to this example. For instance, another arrangement is acceptable in which, without using the FB pulse, the degree of recovery of the signal value in the image taking region is determined on the basis of a cumulative value of signal values in the monitor region. Thus, in the following sections, an example of this arrangement will be explained as a fourth embodiment.

In the fourth embodiment, similarly to the embodiment described above, the executing function 13a executes the pulse sequence to acquire the data from the image taking region after applying the pre-pulse that changes the longitudinal magnetization of the nuclear spin into a negative value, in synchronization with a predetermined cardiac phase of the subject. Further, every time a predetermined ECG waveform occurs, the executing function 13a acquires data from a monitor region which is different from the image taking region and to which a pre-pulse is applied at the same time as a pre-pulse is applied to the image taking region.

For example, similarly to the embodiment described above, the executing function 13a executes the pulse sequence in synchronization with R-waves of the subject. Further, every time an R-wave is detected, the executing function 13a acquires data from the monitor region. It should be noted, however, that the executing function 13a does not apply the FB pulse to the monitor region in the fourth embodiment.

Further, in the fourth embodiment, when a cumulative value resulting from accumulating the signal values obtained by the monitoring function 15b is equal to or larger than a predetermined threshold value, the controlling function 15c exercises control so that the pulse sequence is executed in the upcoming predetermined cardiac phase. When the cumulative value of the signal values is smaller than the predetermined threshold value, the controlling function 15c exercises control so that the pulse sequence is not executed in the upcoming predetermined cardiac phase.

In other words, in the fourth embodiment, the controlling function 15c determines that the signal value in the image taking region has sufficiently recovered "when the cumulative value of the signal values in the monitor region has reached the thresholds value", instead of "when the signal value of the monitor region has reached the threshold value" described in the embodiment above.

More specifically, the controlling function 15c accumulates the signal values every time a signal value is obtained by the monitoring function 15b. In other words, the controlling function 15c adds the obtained signal value to the cumulative value of the signal values that have so far been accumulated. After that, the controlling function 15c compares the cumulative signal value with the predetermined threshold value. Subsequently, when the cumulative signal value is equal to or larger than the threshold value, the controlling function 15c controls the executing function 13a so as to execute the pulse sequence at the upcoming R-wave. On the contrary, when the cumulative signal value is smaller than the threshold value, the controlling function 15c controls the executing function 13a so as not to execute the pulse sequence at the upcoming R-wave. In this situation, when the controlling function 15c controls the executing function 13a so as to execute the pulse sequence at the upcoming R-wave, the controlling function 15c initializes the cumulative value of the signal values that have so far been accumulated, to zero.

For example, the controlling function 15c determines whether or not the pulse sequence should be performed on the basis of Expression (1) below, where x denotes the number of times the data acquiring process from the monitor region has been performed, and Sx denotes the signal value obtained by the monitoring function 15b at each time.

$$\Sigma |Sx| \geq \text{Threshold value} \qquad (1)$$

Figure 13:
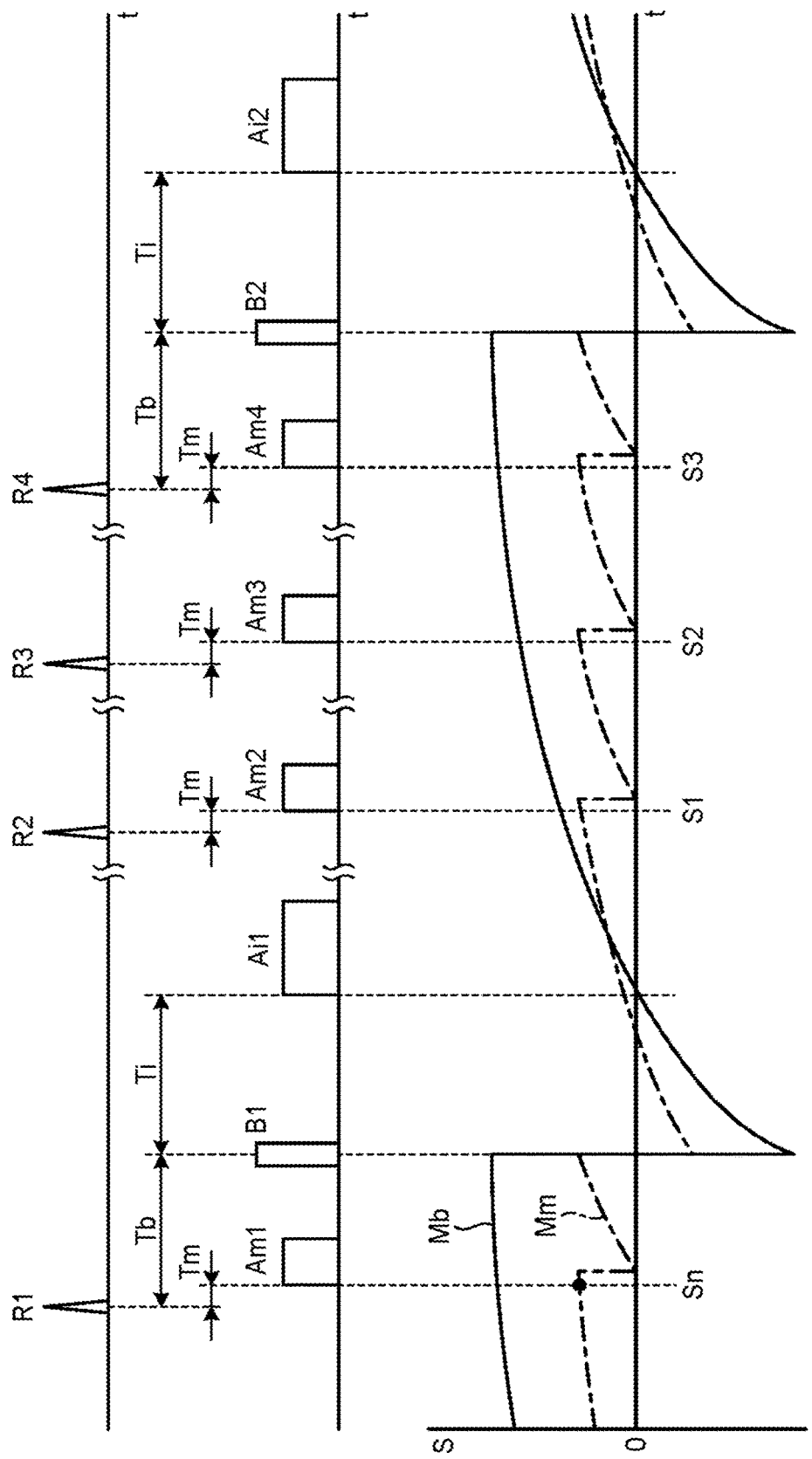
FIG. 13 is a time chart illustrating an example of control realized by a controlling function according to a fourth embodiment.

FIG. 13 is a time chart illustrating an example of the control realized by the controlling function 15c according to the fourth embodiment. In the present example, the diagram in the top section of FIG. 13 illustrates the timing with which R-waves are detected, similarly to the diagram in the top section of FIG. 7. Further, the diagram in the middle section of FIG. 13 illustrates the timing with which the applications of a pre-pulse and the data acquiring processes are performed, similarly to the diagram in the middle section of FIG. 7. Further, the chart in the bottom section of FIG. 13 illustrates fluctuations of the signal values corresponding to the longitudinal magnetization of the blood and to the longitudinal magnetization of the tissue included in the monitor region, similarly to the chart in the bottom section of FIG. 7.

For example, as illustrated in FIG. 13, when the first R-wave (R1) is detected, the executing function 13a performs a data acquiring process (Am1) from the monitor region at the point in time when the time period Tm has elapsed. After that, the controlling function 15c adds the signal value of the data acquired from the monitor region to the cumulative value of the signal values that have so far been accumulated and further compares the cumulative signal value with the predetermined threshold value. In this situation, for example, when the signal value of the data acquired at this point in time is expressed as Sn, let us assume that the value obtained by adding Sn to the cumulative value of the signal values that have so far been accumulated is equal to or larger than the threshold value. In that situation, the controlling function 15c controls the executing function 13a so as to apply a BB pulse (B1) at the time when the time period Tb has elapsed since the first R-wave (R1). As a result, it means that the application of the BB pulse (B1) and the data acquiring process (Ai1) from the image taking region are performed in synchronization with the first R-wave (R1). In that situation, the controlling function 15c initializes the cumulative value of the signal values to zero.

Further, as illustrated in FIG. 13, when the second R-wave (R2) is detected, the executing function 13a performs a data acquiring process (Am2) from the monitor region at the point in time when the time period Tm has elapsed, similarly to the situation with the first R-wave (R1). After that, the controlling function 15c adds the signal value of the data acquired from the monitor region to the cumulative value of the signal values that have so far been accumulated and further compares the cumulative signal value obtained in this manner with the predetermined threshold value. In this situation, for example, when the signal value of the data acquired at this point in time is expressed as S1, because the cumulative value of the signal values that have so far been accumulated is initialized to zero, the calculated value is equal to S1. In this situation, for example, let us discuss an example in which S1 is smaller than threshold value. In that situation, the controlling function 15c controls the executing function 13a so as not to apply a BB pulse. As a result, neither the application of a BB pulse nor a data acquiring process from the image taking region is performed at the second R-wave (R2). In this situation, the controlling function 15c does not initialize the cumulative signal value that was calculated.

Further, as illustrated in FIG. 13, when the third R-wave (R3) is detected, the executing function 13a performs a data acquiring process (Am3) from the monitor region at the point in time when the time period Tm has elapsed, similarly to the situations with the first and the second R-waves (R1 and R2). After that, the controlling function 15c adds the signal value of the data acquired from the monitor region to the cumulative value of the signal values that have so far been accumulated and further compares the cumulative signal value obtained in this manner with the predetermined threshold value. In this situation, for example, when the signal value of the data acquired at this point in time is expressed as S2, because the cumulative value of the signal values that have so far been accumulated is S1, the calculated value is equal to S1+S2. In this situation, let us discuss an example in which S1+S2 is smaller than the threshold value. In that situation, the controlling function 15c controls the executing function 13a so as not to apply a BB pulse. As a result, neither the application of a BB pulse nor a data acquiring process from the image taking region is performed, also at the third R-wave (R3). In this situation also, the controlling function 15c does not initialize the cumulative signal value that was calculated.

Further, as illustrated in FIG. 13, when the fourth R-wave (R4) is detected, the executing function 13a performs a data acquiring process (Am4) from the monitor region at the point in time when the time period Tm has elapsed. After that, the controlling function 15c adds the signal value of the data acquired from the monitor region to the cumulative value of the signal values that have so far been accumulated and further compares the cumulative signal value obtained in this manner with the predetermined threshold value. In this situation, for example, when the signal value of the data acquired at this point in time is expressed as S3, because the cumulative value of the signal values that have so far been accumulated is S1+S2, the calculated value is equal to S1+S2+S3. In this situation, let us discuss an example in which S1+S2+S3 is equal to or larger than the threshold value. In that situation, the controlling function 15c controls the executing function 13a so as not to apply a BB pulse (B2) at the time when the time period Tb has elapsed since the fourth R-wave (R4). As a result, the application of the BB pulse (B2) and a data acquiring process (Ai2) from the image taking region are performed in synchronization with the fourth R-wave (R4). In this situation, the controlling function 15c initializes the cumulative signal value to zero.

As explained above, the controlling function 15c controls the execution of the pulse sequence on the basis of the cumulative value of the signal values of the pieces of data acquired from the monitor region. In this situation, the nuclear spin in the monitor region is brought into a transverse magnetization state by an excitation-purpose RF pulse every time a data acquiring process is performed; however, immediately after going into the transverse magnetization state, the longitudinal magnetization gradually recovers according to a longitudinal relaxation time period. For this reason, by calculating the cumulative value of the signal values of the data acquired from the monitor region, it is possible to understand the degree of recovery of the longitudinal magnetization in the image taking region, similarly to the example in the embodiment described above in which the fluctuation of the signal value of the data acquired from the monitor region is monitored.

In the fourth embodiment also, to cope with situations where R-waves occur successively at short intervals therebetween as observed in bigeminy, the executing function 13a exercises control so that, when a plurality of R-waves occur successively within a predetermined time period, only the R-wave occurring the first during the time period is adopted. For example, the executing function 13a performs a data acquiring process (Am) from the monitor region at the point in time when the time period Tm has elapsed since the point in time when an R-wave is detected. During the time period from the point in time when the data acquiring process (Am) is performed to the time when the data acquiring process (Am) is completed, the executing function 13a exercises control so that a data acquiring process (Am) is not performed even if the next R-wave occurs.

FIG. 14 is a flowchart illustrating a processing procedure according to an image taking method implemented by the MRI apparatus 100 according to the fourth embodiment. For example, as illustrated in FIG. 14, in the MRI apparatus 100, when the ECG circuitry 17 detects an R-wave (step S201: Yes), the executing function 13a acquires data from the monitor region (step S202). In this situation, the executing function 13a stands by without acquiring any data from the monitor region until another R-wave is detected (step S201: No).

Further, when the executing function 13a has acquired the data from the monitor region, the monitoring function 15b obtains the signal value of the data from the monitor region (step S203). After that, when the monitoring function 15b has obtained the signal value of the data from the monitor region, the controlling function 15c accumulates the signal values obtained by the monitoring function 15b (step S204) and further compares the cumulative signal value with the predetermined threshold value (step S205).

In this situation, when the cumulative signal value is equal to or larger than the threshold value (step S205: Yes), the controlling function 15c initializes the cumulative signal value to zero (step S206) and further controls the executing function 13a so as to acquire data from the image taking region after applying a BB pulse (steps S207 and S208). On the contrary, when the signal value is smaller than the threshold value, the controlling function 15c controls the executing function 13a so as not to perform the application of a BB pulse and the data acquiring process from the image taking region and stands by until the next time when a signal value of data from the monitor region is obtained (step S205: No).

In this manner, the controlling function 15c controls the executing function 13a so as to repeatedly perform a data acquiring process from the image taking region until the data is acquired from all the segments (step S209: No). Subsequently, when the controlling function 15c has acquired the data from all the segments (step S209: Yes), the image generating function 14a generates an image on the basis of the acquired data (step S210).

In the present example, steps S201 through S202 are steps realized as a result of the processing circuitry 13 invoking the predetermined program corresponding to the executing function 13a from the storage circuitry 11 and executing the invoked program. Step S203 is a step realized as a result of the processing circuitry 15 invoking the predetermined program corresponding to the monitoring function 15b from the storage circuitry 11 and executing the invoked program. Steps S204 through S209 are steps realized as a result of the processing circuitry 15 invoking the predetermined program corresponding to the controlling function 15c from the storage circuitry 11 and executing the invoked program.

Further, step S210 is a step realized as a result of the processing circuitry 14 invoking the predetermined program corresponding to the image generating function 14a from the storage circuitry 11 and executing the invoked program.

As explained above, in the fourth embodiment, by calculating the cumulative value of the signal values of the data acquired from the monitor region, it is possible to understand the degree of recovery of the longitudinal magnetization in the image taking region. Accordingly, similarly to the embodiment described above, it is possible to acquire the data from the image taking region with appropriate timing even when the intervals of the R-waves become shorter and even when the intervals of the R-waves become longer due to arrhythmia. In other words, it is possible to acquire appropriate data regardless of whether or not arrhythmia occurs.

OTHER EMBODIMENTS

For example, in the embodiment described above, the example is explained in which the executing function 13a acquires data from the monitor region every time the predetermined ECG waveform occurs; however, possible embodiments are not limited to this example. For instance, the executing function 13a may acquire data from the monitor region, by using timing excluding the time periods during which data is acquired from the image taking region. In that situation, for example, the executing function 13a acquires data from the monitor region regularly at predetermined intervals, on the basis of a clock signal generated by the processor included in the processing circuitry 13, by using timing excluding the time periods during which the data is acquired from the image taking region.

Further, for example, in the embodiment described above, the example is explained in which the executing function 13a executes the pulse sequence in synchronization with the trigger signal output from the ECG circuitry 17; however, possible embodiments are not limited to this example. For instance, the executing function 13a may execute the pulse sequence in synchronization with a trigger signal output from a plethysmograph attached to the subject.

Further, in the embodiment described above, the example using the pre-pulse called BB pulse is explained; however, possible embodiments are not limited to this example. For example, the same embodiment is applicable to situations involving any of other types of pre-pulses that change the longitudinal magnetization of a nuclear spin into a negative value, such as a so-called inversion pulse or a pre-pulse used for suppressing the background. In those situations, the flip angle of the RF pulse used as a pre-pulse does not necessarily have to be 180° and may be any angle that is equal to or larger than 90° and is smaller than 180°.

In the embodiment described above, the example is explained in which the T2-weighted image of the heart is taken; however, possible embodiments are not limited to this example. For instance, the same embodiment is applicable to situations where another image taking method using a pre-pulse is implemented, such as a delayed enhancement imaging process performed on the heart or a T1 map imaging process performed on the heart. When performing any of these imaging processes, it is also desirable to set a monitor region so as to include cerebrospinal fluid in the spine of the subject, for example. Further, for example, when performing a T1 map imaging process is performed, the pre-pulse does not necessarily have to be configured to change the longitudinal magnetization of a nuclear spin into a negative value. The pre-pulse may be configured to change the longitudinal magnetization into a value equal to or larger than zero, as long as it is possible to observe fluctuations of the longitudinal magnetization.

Further, in the embodiment described above, it is also acceptable to provide the first heartbeat with a dummy segment on which no data acquiring process is performed. When using the dummy segment in the present example, when the first R-wave of the subject is detected, for instance, the controlling function 15c controls the executing function 13a so as to unconditionally apply a BB pulse without acquiring any data from the monitor region, and also, so as not to acquire any data from the image taking region. Further, at the second and later R-waves, the controlling function 15c acquires data from the monitor region as explained in the embodiment above and controls the execution of the pulse sequence on the basis of the signal values of the acquired pieces of data. In other words, in this situation, the pieces of data acquired from the image taking region at the second and later heartbeats will be used for the generation of an image.

As explained above, by providing the first heartbeat with the dummy segment, it is possible to arrange the fluctuations of the signal values of the pieces of data acquired from the monitor region and from the image taking region at the second and later heartbeats to match the fluctuations of the longitudinal magnetization that are expected in advance as illustrated in FIGS. 7 and 13, for example. With this arrangement, it is possible to stabilize the signal values of the pieces of data acquired at the second and later heartbeats, and it is therefore possible to further improve the quality of the generated image.

In the embodiment described above, the example is explained in which the pre-pulses are applied to the image taking region and to the monitor region at the same time; however, possible embodiments are not limited to this example. For instance, the timing with which a pre-pulse is applied to the image taking region and the timing with which a pre-pulse is applied to the monitor region may be different from each other by a certain length of time, as long as both of the pre-pulses are applied in synchronization with a predetermined ECG waveform of the subject. Because the longitudinal relaxation time period of a nuclear spin is determined in a fixed manner for each tissue, even if the pre-pulses are applied with mutually-different timing schemes, it is considered that the signal from the image taking region and the signal from the monitor region should be in certain correlation with each other, as long as the difference therebetween is constant. Accordingly, even if the timing with which the pre-pulse is applied to the image taking region and the timing with which the pre-pulse is applied to the monitor region are different from each other by a certain length of time, it is possible to understand the degree of recovery of the longitudinal magnetization in the image taking region, on the basis of a fluctuation of the signal value of the data acquired from the monitor region.

According to at least one aspect of the embodiments described above, it is possible to obtain an image with excellent quality even if the cardiac cycle is disturbed by arrhythmia or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalent are intended to cover such forms or modifications as would fall within the scope and spirit of the inventions.

What is claimed is:

1. A magnetic resonance imaging apparatus comprising:
processing circuitry configured to execute a pulse sequence to acquire data from an image taking region after applying a first pre-pulse to the image taking region in synchronization with a predetermined electrocardiographic waveform of a subject, wherein
the processing circuitry is further configured to:
acquire data from a monitor region that is different from the image taking region after applying a second pre-pulse to the monitor region, by using timing linked with timing with which the first pre-pulse is applied;
monitor a degree of recovery of longitudinal magnetization in the data acquired from the monitor region; and
control execution of the pulse sequence in accordance with the degree of recovery of longitudinal magnetization.

2. The magnetic resonance imaging apparatus according to claim 1, wherein the monitor region is set so as to include a tissue of which a longitudinal relaxation time period is equal to or longer than a longitudinal relaxation time period of a tissue of which a signal value is suppressed by the first pre-pulse.

3. The magnetic resonance imaging apparatus according to claim 1, wherein the processing circuitry exercises control so that, when a signal value of the longitudinal magnetization is equal to or larger than a predetermined threshold value, the pulse sequence is executed with an upcoming predetermined electrocardiographic waveform and exercises control so that, when the signal value of the longitudinal magnetization is smaller than the predetermined threshold value, the pulse sequence is not executed with the upcoming predetermined electrocardiographic waveform.

4. The magnetic resonance imaging apparatus according to claim 1, wherein the processing circuitry further receives, from an operator, an operation to designate a range within an image of the subject being displayed on a display and sets the monitor region on a basis of the designated range.

5. The magnetic resonance imaging apparatus according to claim 1, wherein
the processing circuitry is configured to:
acquire data from the monitor region every time the predetermined electrocardiographic waveform occurs, and
every time data is acquired from the monitor region, obtain a signal value of the acquired data.

6. The magnetic resonance imaging apparatus according to claim 1, wherein
the processing circuitry is configured to:
acquire the data from the monitor region by using tuning excluding a time period during which the data is acquired from the image taking region, and
every time data is acquired from the monitor region, obtain a signal value of the acquired data.

7. The magnetic resonance imaging apparatus according to claim 3, wherein
the processing circuitry is configured to set a time period from a time when the predetermined electrocardiographic waveform is detected to a time when the first pre-pulse is applied, in accordance with how large a difference is between the signal value and the predetermined threshold value.

8. The magnetic resonance imaging apparatus according to claim 1, wherein the image taking region is set so as to include a myocardium of the subject.

9. The magnetic resonance imaging apparatus according to claim 1, wherein the monitor region is set so as to include cerebrospinal fluid of the subject.

10. The magnetic resonance imaging apparatus according to claim 1, wherein the first pre-pulse is a pre-pulse configured to change longitudinal magnetization of a nuclear spin into a negative value.

11. A magnetic resonance imaging method comprising:
executing a pulse sequence to acquire data from an image taking region after applying a first pre-pulse to the image taking region in synchronization with a predetermined electrocardiographic waveform of a subject wherein
the executing of the pulse sequence includes:
acquiring data from a monitor region that is different from the image taking region after applying a second pre-pulse to the monitor region, by using timing linked with timing with which the first pre-pulse is applied;
monitoring a degree of recovery of longitudinal magnetization in the data acquired from the monitor region; and
controlling execution of the pulse sequence in accordance with the degree of recovery of longitudinal magnetization.

* * * * *